United States Patent
Biedermann et al.

(10) Patent No.: US 10,271,877 B2
(45) Date of Patent: Apr. 30, 2019

(54) COUPLING DEVICE FOR COUPLING A ROD TO A BONE ANCHORING ELEMENT AND BONE ANCHORING DEVICE WITH SUCH A COUPLING DEVICE

(71) Applicant: BIEDERMANN TECHNOLOGIES GMBH & CO. KG, Donaueschingen (DE)

(72) Inventors: Lutz Biedermann, VS-Villingen (DE); Timo Biedermann, Trossingen (DE); Wilfried Matthis, Weisweil (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 0 days.

(21) Appl. No.: 15/818,278

(22) Filed: Nov. 20, 2017

(65) Prior Publication Data

US 2018/0132903 A1    May 17, 2018

Related U.S. Application Data

(63) Continuation of application No. 15/152,044, filed on May 11, 2016, now Pat. No. 9,839,446.
(Continued)

(30) Foreign Application Priority Data

May 12, 2015    (EP) ..................... 15167435

(51) Int. Cl.
*A61B 17/70*    (2006.01)
*A61B 17/56*    (2006.01)
*A61B 17/68*    (2006.01)

(52) U.S. Cl.
CPC .... *A61B 17/7037* (2013.01); *A61B 2017/567* (2013.01); *A61B 2017/681* (2013.01)

(58) Field of Classification Search
CPC .......... A61B 17/7037; A61B 2017/567; A61B 2017/681
(Continued)

(56) References Cited

U.S. PATENT DOCUMENTS

| 5,882,350 A | 3/1999 | Ralph et al. |
| 6,248,105 B1 | 6/2001 | Schläpfer et al. |

(Continued)

FOREIGN PATENT DOCUMENTS

EP    2 851 021 A1    3/2015

OTHER PUBLICATIONS

European Search Report dated Nov. 17, 2015 for Application No. 15167435.5; (7 Pages).

*Primary Examiner* — Kevin T Truong
*Assistant Examiner* — David C Comstock
(74) *Attorney, Agent, or Firm* — Lewis Roca Rothgerber Christie LLP

(57) ABSTRACT

A coupling device is provided for coupling a rod to a bone anchoring element. The coupling device includes a receiving part having a first end, a second end, a central axis extending through the first end and the second end, and a channel for receiving a rod. The receiving part defines an accommodation space for accommodating a head of a bone anchoring element, the accommodation space having an opening for inserting the head. The coupling device further includes a pressure element arranged at least partially in the accommodation space, the pressure element having a flexible portion to clamp an inserted head, and a clamping element extending at least partially around the flexible portion of the pressure element. The clamping element is configured to move from a first position to a second position in which the clamping element exerts a clamping force onto the pressure (Continued)

element, where the movement includes rotating the clamping element around the central axis.

20 Claims, 20 Drawing Sheets

Related U.S. Application Data

(60) Provisional application No. 62/160,479, filed on May 12, 2015.

(58) Field of Classification Search
USPC .......................................... 606/266–270, 272
See application file for complete search history.

(56) References Cited

U.S. PATENT DOCUMENTS

| | | |
|---|---|---|
| 8,506,609 B2 | 8/2013 | Biedermann et al. |
| 8,888,827 B2 * | 11/2014 | Harper ............... A61B 17/7056 606/305 |
| 8,926,671 B2 | 1/2015 | Biedermann et al. |
| 8,951,294 B2 | 2/2015 | Gennari et al. |
| 9,839,446 B2 * | 12/2017 | Biedermann ...... A61B 17/7037 |
| 2007/0167949 A1 | 7/2007 | Altarac et al. |
| 2010/0234902 A1 * | 9/2010 | Biedermann ...... A61B 17/7032 606/305 |
| 2012/0046701 A1 | 2/2012 | Gennari et al. |
| 2013/0096622 A1 | 4/2013 | Biedermann et al. |
| 2013/0096623 A1 | 4/2013 | Biedermann et al. |
| 2014/0188173 A1 | 7/2014 | Mishra et al. |
| 2014/0257411 A1 | 9/2014 | Rezach |

* cited by examiner

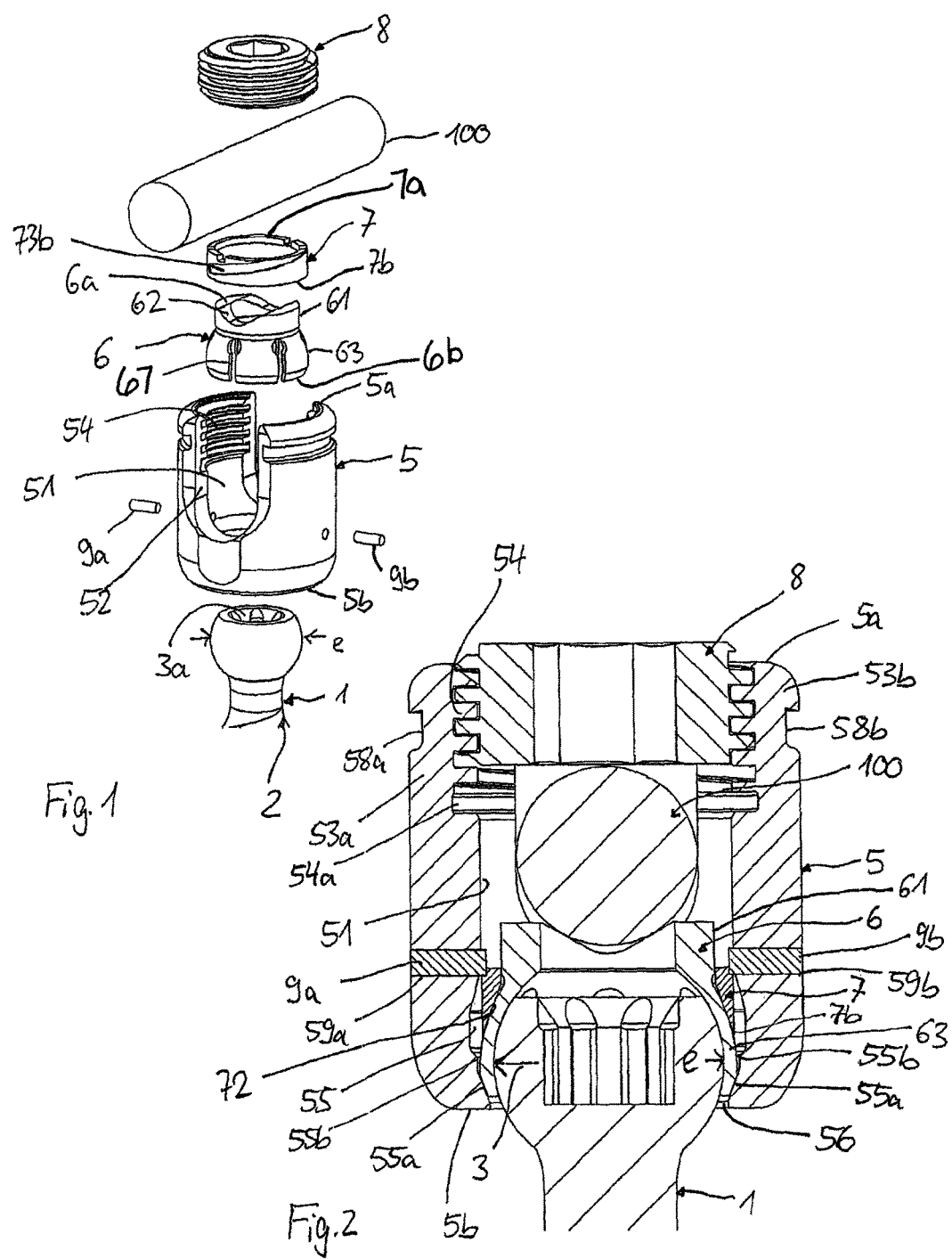

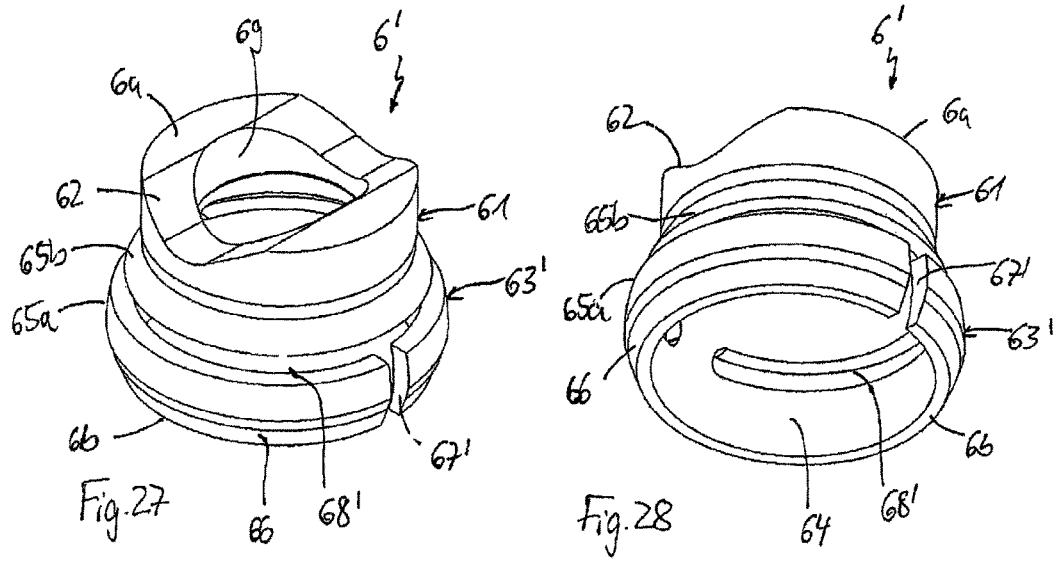
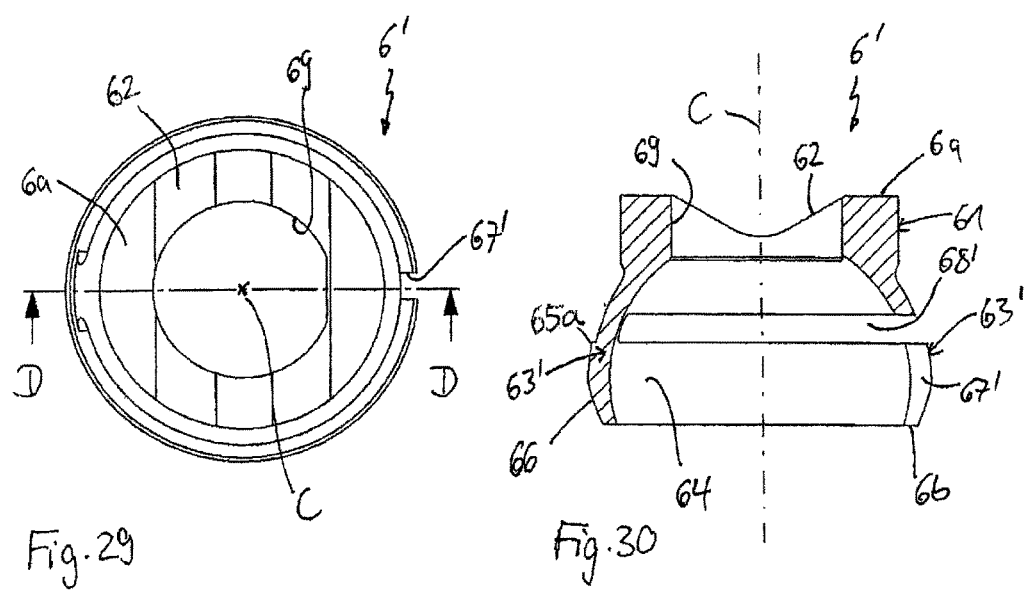

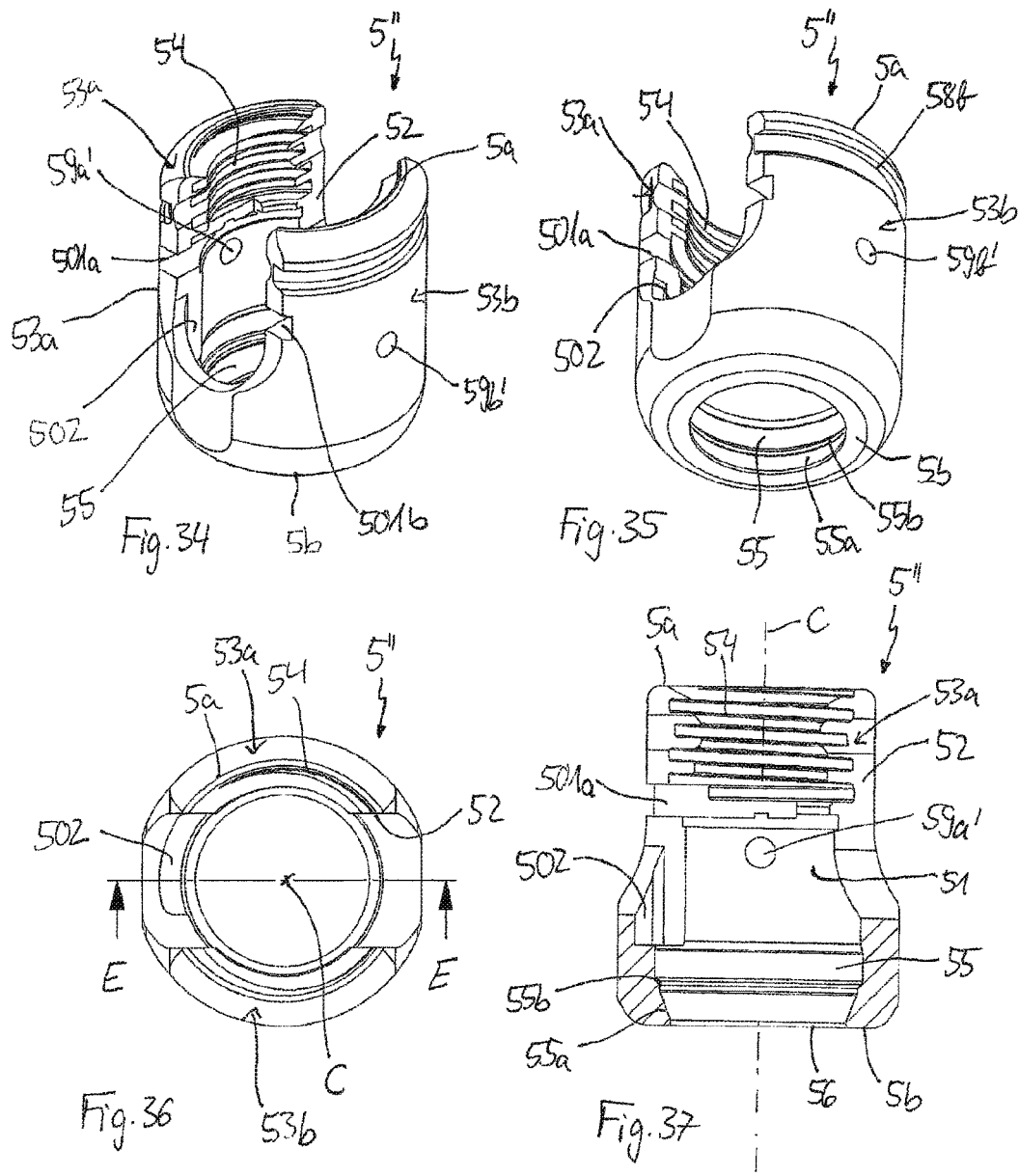

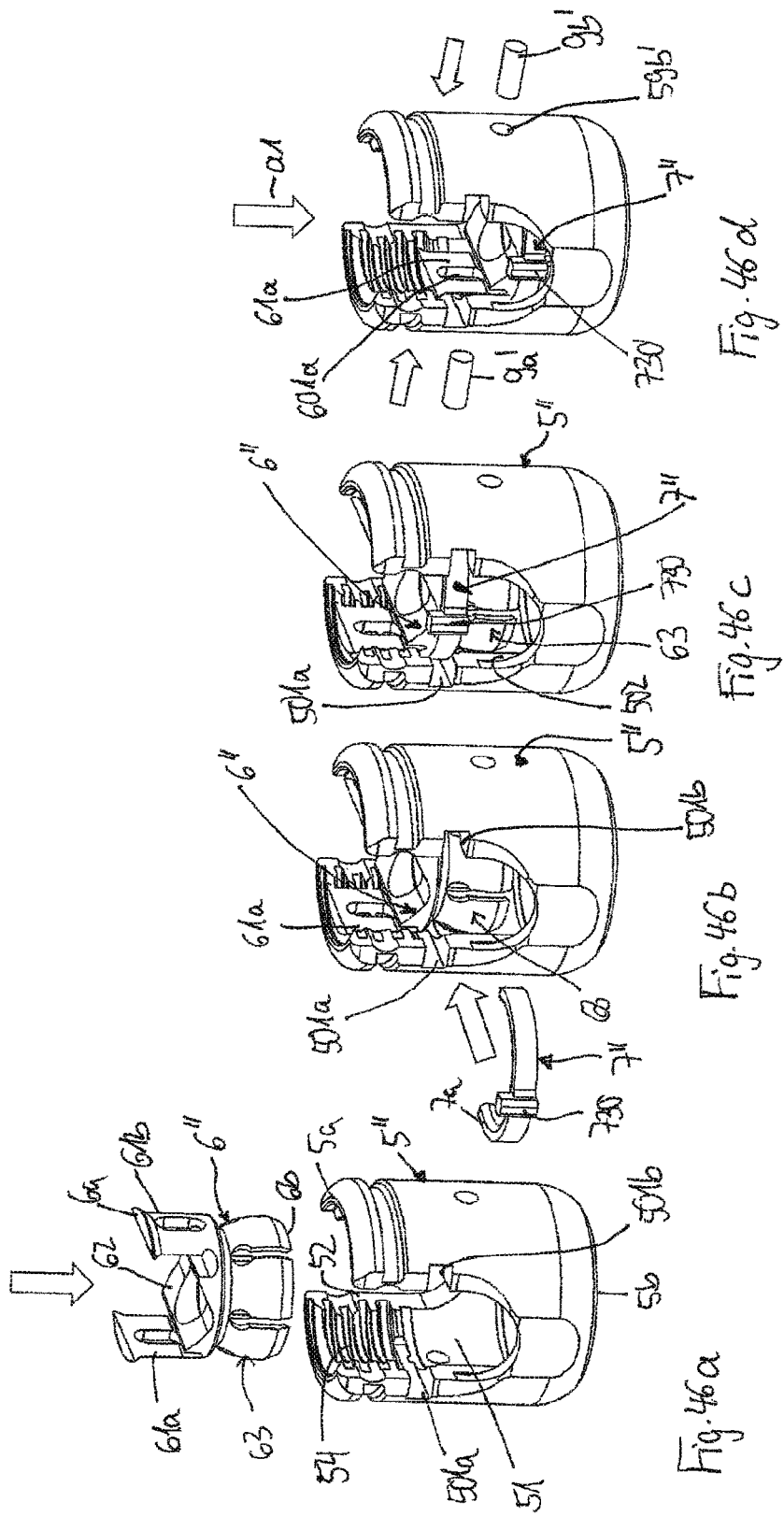

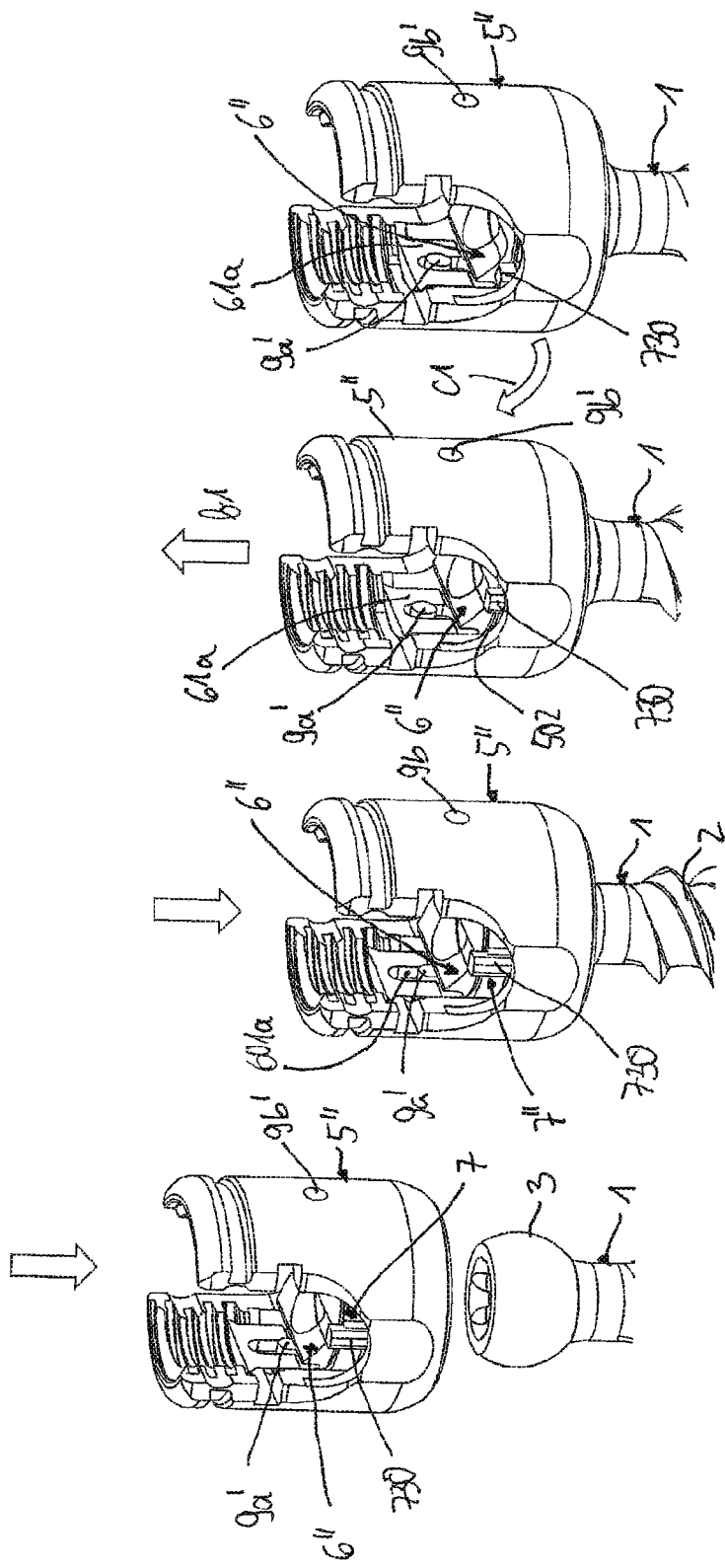

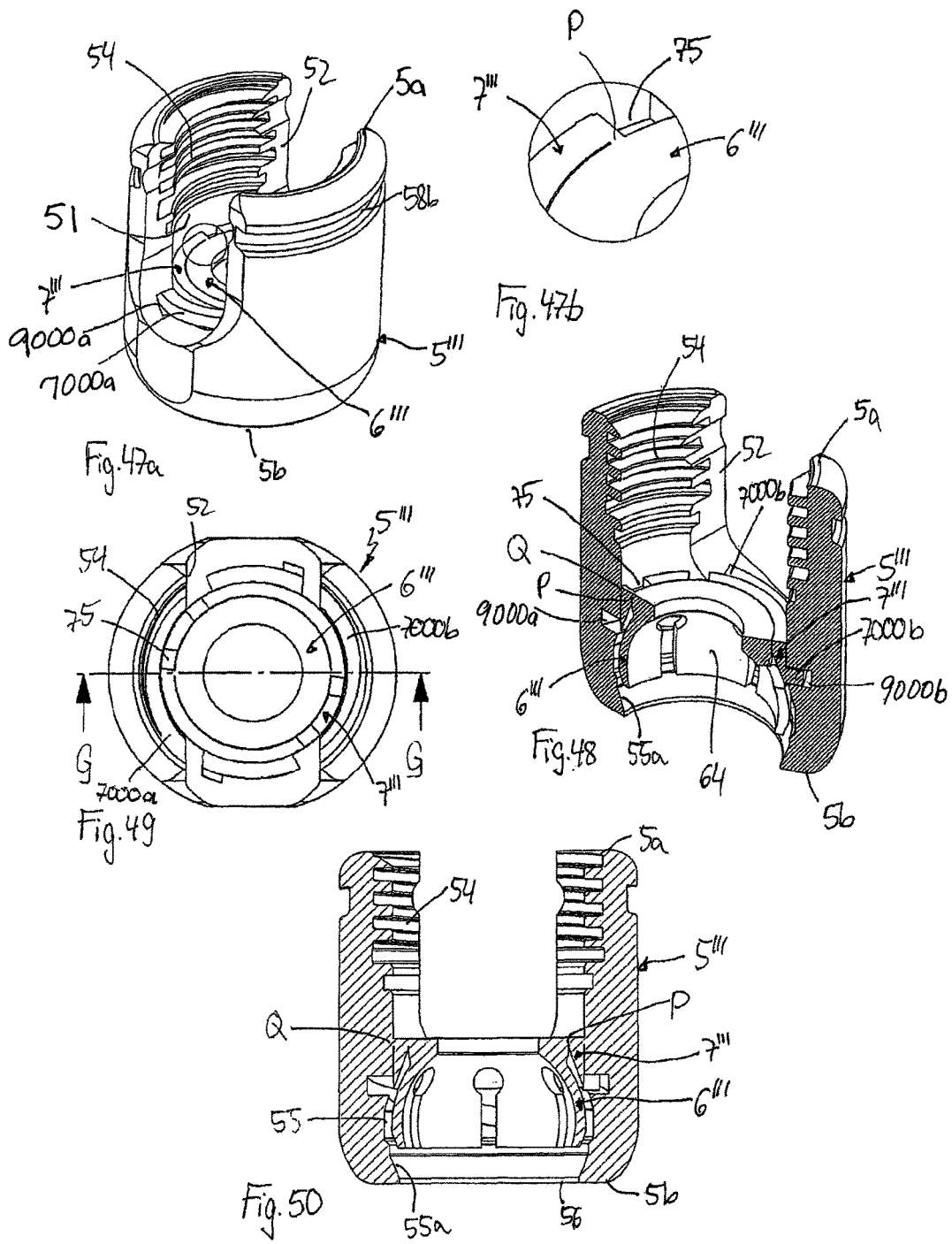

COUPLING DEVICE FOR COUPLING A ROD TO A BONE ANCHORING ELEMENT AND BONE ANCHORING DEVICE WITH SUCH A COUPLING DEVICE

CROSS-REFERENCE TO RELATED APPLICATIONS

This application is a continuation of U.S. patent application Ser. No. 15/152,044, filed May 11, 2016, which claims the benefit of U.S. Provisional Application Ser. No. 62/160,479, filed May 12, 2015, the contents of which are hereby incorporated by reference in their entirety, and claims priority from European Patent Application EP 15 167 435.5, filed May 12, 2015, the contents of which are hereby incorporated by reference in their entirety.

BACKGROUND

Field

The present disclosure relates to a coupling device for coupling a rod to a bone anchoring element. The coupling device includes a receiving part for receiving a rod and for coupling the rod to a bone anchoring element. The receiving part is configured to accommodate a head of a bone anchoring element such that the head can pivot with respect to the receiving part. The coupling device further includes a pressure element with a flexible portion to clamp a head inserted therein and a clamping element configured to exert a compression force onto the pressure element to increase a friction force between the pressure element and the head.

Description of the Related Art

U.S. Pat. No. 8,926,671 describes a receiving part for receiving a rod and for coupling the rod to a bone anchoring element. The receiving part includes a receiving part body for accommodating a head of the bone anchoring element and a pressure element with a flexible portion to clamp an inserted head. The pressure element is movable along a longitudinal axis of the receiving part body from an insertion position where the head is insertable into the receiving part body to a pre-locking position where the head is clamped in the receiving part body by a pre-stress exerted by the pressure element. The pressure element is further movable to a locking position where the head is locked in the receiving part body. The pre-stress exerted by the pressure element allows a desired angular position of the bone anchoring element to be maintained relative to the receiving part by friction before the head of the bone anchoring element is finally locked.

U.S. Pat. No. 6,248,105 B1 describes a device for connecting a longitudinal rod with a bone anchoring element, such as a pedicle screw, thereby forming a fixation system for the spine. The device includes a connecting member accepting a longitudinal rod. A radially compressible spring chuck is arranged within the connecting member that has a cavity for receiving a head of the bone anchoring element. An insert slides into a bore hole of the connecting member and has a recess with a complementarily conical shape to a conical shape of the spring chuck. The insert radially compresses the spring chuck at an interface between the conical shapes and therewith fastens the head of the pedicle screw.

U.S. Pat. No. 8,951,294 B2 describes a spinal implant with an anchoring part and a mounting part with an internal axial housing to transversely receive a connecting rod. The spinal implant includes retaining elements that are situated near the bottom of the axial housing of the mounting part. The retaining elements are adapted to fasten a locking member in a stationary locking position in which a ball joint connection, formed by first and second connecting elements, is locked to fasten the anchoring part and the mounting part in rotation relative to each other about at least two orthogonal axes.

US 2013/0096622 A1 describes a polyaxial bone anchoring device having a pressure element that exerts pressure onto a head of an anchoring element. The pressure element maintains the head in an adjustable angular position relative to a receiving part by friction using threaded set screws. A desired friction force can be achieved by controlling the thread turning and advancement of the set screws.

SUMMARY

Embodiments of the invention provide an improved coupling device and an improved bone anchoring device that facilitates handling during surgery.

The coupling device allows adjusting a friction force exerted on a head of a bone anchoring element in an easy manner during surgery. The coupling device may be particularly useful for a polyaxial bone anchoring element of the bottom loading type, where the head of the bone anchoring element is inserted into a receiving part from a bottom end thereof. More particularly, the coupling device allows the receiving part to be placed onto a head of a bone anchoring element in-situ, after a shaft of the bone anchoring element has already been inserted into a bone. Hence, in one or more embodiments, an in-situ type bottom loading bone anchoring element is provided, where a friction force acting onto the head can be increased by actuating a clamping element of the coupling device. By frictional clamping of the head before final locking of the bone anchoring device, the procedure of aligning a plurality of receiving parts for inserting a rod is considerably simplified.

In one embodiment, the clamping element cooperates with a portion of the receiving part according to a bayonet-like locking advancement structure, where an engagement member, such as a pin, engages a helical groove that allows the clamping element to advance in an axial direction while rotating. The advancement is stepless, thereby providing a stepless adjustment of the clamping force onto the head. The interaction between the engagement member and the helical groove may be self-locking such that a desired position of the clamping element relative to the receiving part can be selected and secured against inadvertent movement.

In another embodiment, an advancement structure that permits an axial advancement of the clamping element is formed by a threaded connection between the clamping element and the receiving part. The advancement structure also allows the clamping element to advance relative to the receiving part in a stepless manner and to adjust the friction force acting on the pressure element in a stepless manner. A pitch of the threaded connection may be the same as a pitch of a threaded connection between the receiving part and a locking element such that the clamping element can be screwed into the receiving part in the same manner as the locking element.

In a further embodiment, the clamping element is an open ring similar to a snap ring that can exert a compression force onto the pressure element when the clamping element is placed around the pressure element. The clamping element has protrusions at a side of the clamping element facing the pressure element. In a first condition, the protrusions rest in recesses of the pressure element. In a second condition, the protrusions are moved out of the recesses thereby enhancing the clamping force on the pressure element. Hence, the clamping force can be increased with only a minimal movement of the clamping element.

The pressure element may have at least one longitudinal slot providing a flexible portion for clamping the head. In one embodiment, the pressure element may have an additional horizontal slot to reduce an insertion force of the head into the pressure element.

In a still further embodiment, the pressure element, the clamping element, and preferably also the receiving part are manufactured as a monolithic piece. In this embodiment, the connection between the pressure element and the clamping element and preferably also the connection between the clamping element and the receiving part each have at least one predetermined breaking point. By exerting a force, for example by rotating the clamping element, the connection breaks at the predetermined breaking point. Thereafter, the pieces are separate parts. An additive manufacturing method can be used to manufacture the monolithic pieces, such as laser sintering or electron beam melting. Thereby, sophisticated structures may be produced.

BRIEF DESCRIPTION OF THE DRAWINGS

Further features and advantages will become apparent from the description of embodiments by means of the accompanying drawings. In the drawings:

FIG. 1 shows an exploded perspective view of a first embodiment of a bone anchoring device with a first embodiment of a coupling device;

FIG. 2 shows a cross-sectional view of the bone anchoring device of FIG. 1 in an assembled state, the cross-section taken in a plane perpendicular to a rod axis;

FIG. 27 shows a perspective view from above a pressure element of the coupling device according to the third embodiment of FIGS. 24 to 26;

FIG. 28 shows a perspective view from below the pressure element of FIG. 27;

FIG. 29 shows a top view of the pressure element of FIGS. 27 and 28;

FIG. 30 shows a cross-sectional view of the pressure element of FIGS. 27 to 29, the cross-section taken along line D-D in FIG. 29;

FIG. 34 shows a perspective view from above a receiving part of the coupling device of FIGS. 31 to 33;

FIG. 35 shows a perspective view from below the receiving part of FIG. 34;

FIG. 36 shows a top view of the receiving part of FIGS. 34 and 35;

FIG. 37 shows a cross-sectional view of the receiving part of FIGS. 34 to 36, the cross-section taken along line E-E in FIG. 36;

FIGS. 46a to 46d show steps of mounting the pressure element and the clamping element to the receiving part according to the fourth embodiment of FIGS. 31 to 45;

FIGS. 46e to 46h show steps of mounting the coupling device according to the fourth embodiment of FIGS. 31 to 45 onto a bone anchoring element and adjusting a friction force onto an inserted head with the clamping element;

FIG. 47a shows a perspective view from above a fifth embodiment of a coupling device;

FIG. 47b shows an enlarged view of a detail of FIG. 47a;

FIG. 48 shows a cross-sectional view of the coupling device of the fifth embodiment of FIGS. 47a and 47b;

FIG. 49 shows a top view of the coupling device of FIGS. 47a to 48; and

FIG. 50 shows a cross-sectional view of the coupling device of FIGS. 47 to 49, the cross-section taken along line G-G in FIG. 49.

DETAILED DESCRIPTION

Figure 3:
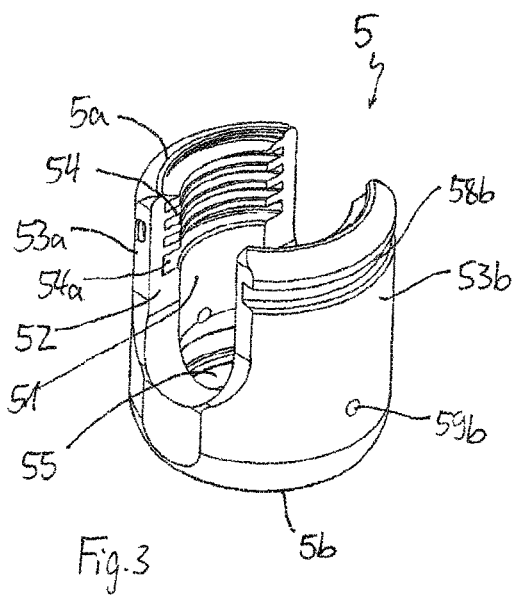
FIG. 3 shows a perspective view from above a receiving part of the coupling device according to the first embodiment of FIGS. 1 and 2.
Figure 4:
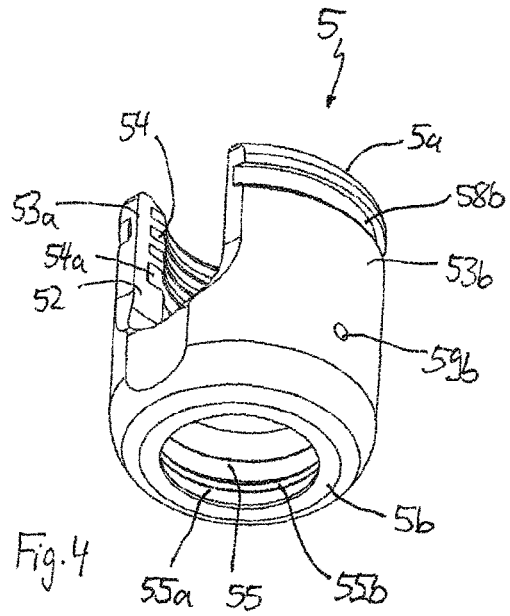
FIG. 4 shows a perspective view from below the receiving part of FIGS. 1 to 3.
Figure 5:
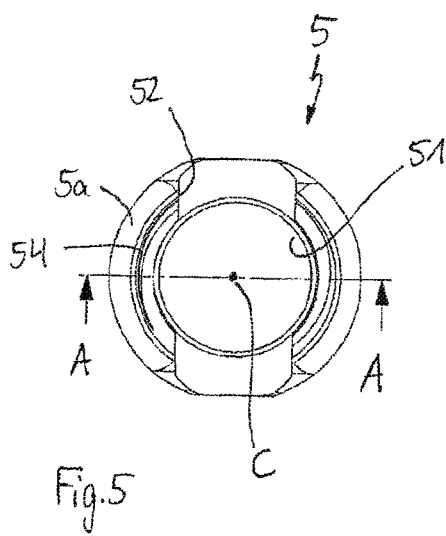
FIG. 5 shows a top view of the receiving part of FIGS. 3 and 4.

As shown in FIGS. 1 and 2, a bone anchoring device according to a first embodiment includes a bone anchoring element 1. The bone anchoring element 1 may be a bone screw having a threaded shaft 2 and a head 3 that may be spherically segment-shaped. The head 3 has a recess 3a for engagement with a screwing-in tool. The bone anchoring device further includes a coupling device for receiving a rod 100 to connect the rod 100 to the bone anchoring element 1. The coupling device includes a receiving part 5 for receiving the rod 100 and the head 3 of the bone anchoring element 1. The coupling device also has a pressure element 6 for exerting a pressure on the head 3 of the bone anchoring element 1 that has been inserted therein to clamp and finally lock the head 3 in the receiving part 5. Additionally, a clamping element 7 is provided for exerting a compression force onto the pressure element 6 to increase the pressure force on the inserted head 3. The bone anchoring device further includes a locking element 8 for securing the rod 100 in the receiving part 5 and for exerting a force to lock the head 3 in the receiving part 5. The locking element 8 may be, for example, a set screw.

The receiving part 5 is now explained with reference to FIGS. 1 to 6. The receiving part 5 includes a first end or proximal end 5a, a second end or distal end 5b opposite the first end 5a, and an axis of symmetry C passing through the first end 5a and the second end 5b. A passage 51 is provided that extends from the first end 5a to the second end 5b and is substantially rotationally symmetric about the axis of symmetry C. In a first region adjacent to the first end 5a, the receiving part 5 has a substantially U-shaped recess 52 that is symmetric with respect to the axis C, the recess 52 having a bottom directed towards the second end 5b. The recess 52 forms two free lateral legs 53a, 53b that extend towards the first end 5a. An internal thread 54 is provided in each of the legs 53a, 53b that cooperates with the locking element 8. The internal thread 54 may be a flat thread (as shown in FIG. 2) to eliminate spreading of the legs 53a, 53b when tightening the locking element 8. The internal thread 54 may, however, have any other suitable thread form. An undercut 54a may be provided at a bottom end of the internal thread 54 (i.e., at an end of the internal thread 54 closest to the second end 5b of the receiving part 5). The undercut 54a may have a depth in a radial direction of the receiving part 5 that is substantially the same as the depth of the thread 54 in the radial direction.

A channel formed by the substantially U-shaped recess 52 is sized to receive the rod 100 therein, where the rod 100 is configured to connect a plurality of anchoring devices.

Figure 6:
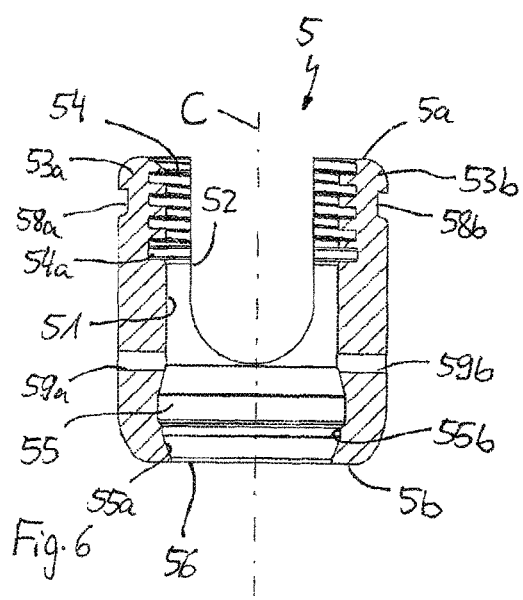
FIG. 6 shows a cross-sectional view of the receiving part of FIGS. 3 to 5, the cross-section taken along line A-A in FIG. 5.
Figure 7:
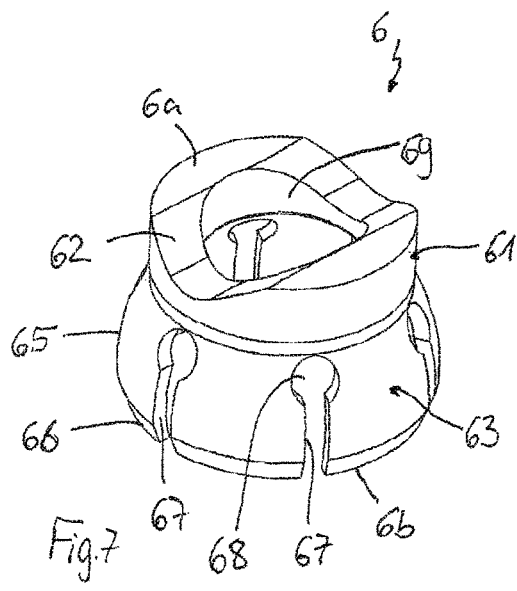
FIG. 7 shows a perspective view from above a pressure element of the coupling device according to the first embodiment of FIGS. 1 and 2.
Figure 8:
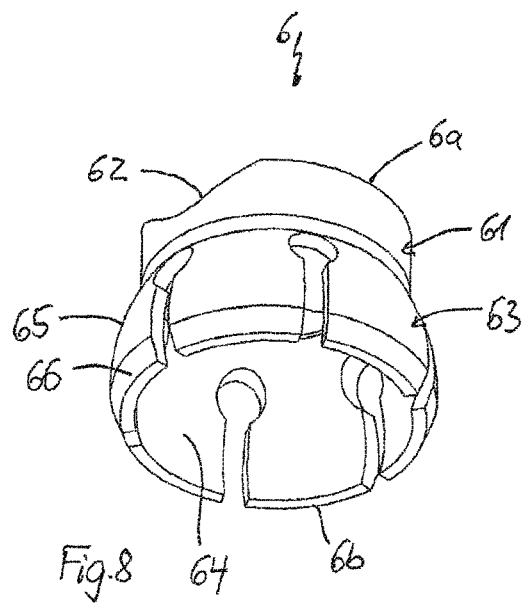
FIG. 8 shows a perspective view from below the pressure element of FIG. 7.
Figure 9:
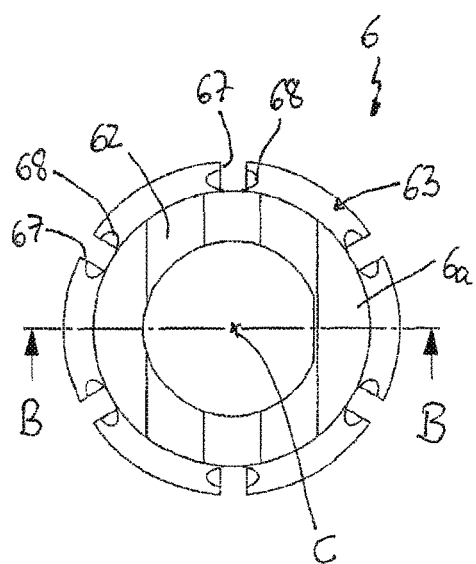
FIG. 9 shows a top view of the pressure element of FIGS. 7 and 8.
Figure 10:
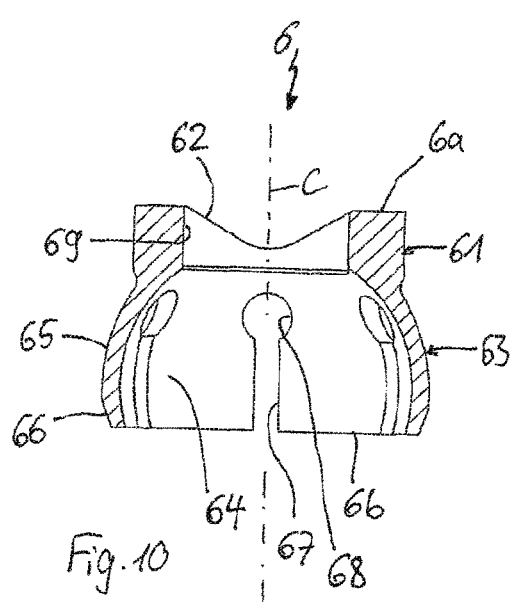
FIG. 10 shows a cross-sectional view of the pressure element of FIGS. 7 to 9, the cross-section taken along line B-B in FIG. 9.

As can be seen in particular in FIGS. 2 and 6, a portion of the passage 51 in an upper section of the receiving part 5 between the first end 5a and approximately the bottom of the U-shaped recess 52 is substantially cylindrical. At approximately the bottom of the U-shaped recess 52, the passage 51 widens, for example conically, to form an accommodation space 55 that has an inner diameter greater than an inner diameter of the passage 51 located in the upper section of the receiving part 5. The accommodation space 55 narrows towards the second end 5b with a narrowing portion 55a extending from a projecting edge 55b to the second end 5b. A size of the accommodation space 55 is such that the head 3 of the bone anchoring element 1 and a lower portion of the pressure element 6 can be accommodated therein. The passage 51 forms an opening 56 at the second end 5b that opens into the accommodation space 55. A diameter of the opening 56 is greater than a greatest diameter of the head 3 such that the head 3 is insertable into the receiving part 5 through the opening 56 at the second end 5b. It should be noted that the narrowing portion 55a can narrow in several shapes, such as a tapered shape as shown in FIGS. 2 and 6, a spherical shape, or can narrow otherwise.

At a distance from the first end 5a, circumferentially extending notches 58a, 58b with downwardly inclined upper and lower surfaces may be provided for engagement with a tool.

On each of the legs 53a, 53b, bores 59a, 59b, extending through the legs 53a, 53b, respectively, are provided for receiving pins 9a, 9b. The bores 59a, 59b are located approximately at a center of each leg 53a, 53b in a circumferential direction of the receiving part 5 and are offset from each other by approximately 180°.

Referring to FIGS. 7 to 10, the pressure element 6 has a first end 6a and an opposite second end 6b. The pressure element 6 is configured to be mounted to the receiving part 5 such that the second end 6b of the pressure element 6 is directed towards the second end 5b of the receiving part 5. The pressure element has a first portion 61 adjacent to the first end 6a that is substantially cylindrical and that has an outer diameter that is smaller than an inner diameter of the passage 51 of the receiving part 5. In the cylindrical first portion 61, a recess with a substantially V-shaped cross-section is formed that provides a rod support surface 62 for supporting an inserted rod 100. The V-shape permits the pressure element 6 to support rods of different diameters. Inserted rods to be supported contact the rod support surface 62 with at least two contact lines extending perpendicular to the cylinder axis of the first portion 61. When the pressure element 6 is in a mounted state in the receiving part 5, the cylinder axis of the first portion 61 coincides with the central axis of symmetry C of the receiving part 5.

A second portion 63 of the pressure element 6 is between the cylindrical first portion 61 and the second end 6b with a hollow interior 64 having a shape adapted to clamp the head 3 therein. In particular, the hollow interior 64 of the second portion 63 has a spherical shape with a length in an axial direction of the pressure element 6 sufficient to accommodate a greatest diameter e of the head 3 therein (see FIG. 2). As described in more detail below, the second portion 63 is open at the second end 6b to allow insertion of the head 3 of the bone anchoring element 1 into the hollow interior 64 from the second end 6b. An outer wall of the second portion 63 includes a first outer surface portion 65 that is substantially spherical and a second outer surface portion 66 adjacent to the second end 6b that narrows towards the second end 6b. In particular, in the embodiment shown, the second outer surface portion 66 is tapered. As can be seen in FIG. 2, a largest outer diameter of the first outer surface portion 65 of the pressure element 6 is smaller than a greatest inner diameter of the accommodation space 55 and greater than an inner diameter of the opening 56 of the receiving part 5. The second portion 63 of the pressure element 6 further has at least one vertical slit 67, preferably a plurality of slits 67, that are open to the second end 6b and extend from a bottom of the second portion 63 almost up to the first portion 61. The at least one vertical slit 67 may widen into a substantially circular enlarged end portion 68 forming a closed end of the slit 67. The enlarged end portion 68 of the slits 67 can have another shape, for example, an oval shape, or any other shape that is different from the slits 67. In some embodiments, the enlarged end portion 68 can be omitted such that each slit 67 has the same width at its closed end as at its respective open end. The number and dimensions of the slits 67 are such that the wall of the second portion 63 is flexible enough to snap onto the head 3 when the head 3 is inserted into the hollow interior 64.

The second portion 63 of the pressure element 6 is a flexible portion that is adapted to exert a pressure onto an inserted head 3 and to hold the head 3 by a frictional force between an inner surface of the hollow interior 64 of the second portion 63 and an outer surface of the head 3. The flexible portion 63 is a cap-like portion that fits tightly onto the head 3. In addition, it shall be noted that the second outer surface portion 66 of the pressure element 6 may have another shape, for example, a rounded shape or any other shape suitable to cooperate with the narrowing portion 55a of the receiving part 5 such that the outer surface portion 66 can be compressed when it enters into the narrowing portion 55a of the receiving part 5.

The pressure element 6 is configured to be inserted into the receiving part 5 through the lower opening 56, whereby the second portion 63 is compressed during insertion. Alternatively, the pressure element 6 may be inserted into the first end 5a of the receiving part 5 and moved downwardly or distally through the passage 51. The outer diameter of the cylindrical first portion 61 of the pressure element 6 is smaller than the inner diameter of the passage 51 such that the clamping element 7 fits there-between. Because the second portion 63 of the pressure element 6 has an outer diameter that is smaller than an inner diameter of the accommodation space 55 and has a flexible wall, the second portion 63 can expand within the accommodation space 55 when the head 3 is inserted into the hollow interior 64 of the pressure element 6.

Further, the pressure element 6 includes a coaxial bore 69 providing access to the head 3 by a tool configured to engage the engagement recess 3a of the head 3.

Referring to FIGS. 11 to 14, the clamping element 7 is a ring-shaped part. The ring is closed and is not flexible. The clamping element 7 has a first end 7a, an opposite second end 7b, and a substantially cylindrical outer shape. As depicted in FIG. 2, the clamping element 7 is configured to be mounted to the receiving part 5 such that the second end 7b of the clamping element 7 is directed towards the second end 5b of the receiving part 5. When the clamping element 7 is in a mounted state in the receiving part 5, the cylinder axis of the clamping element 7 coincides with the central axis of symmetry C of the receiving part 5. As depicted in FIG. 2, an outer diameter of the clamping element 7 is slightly smaller than an inner diameter of the passage 51 in the upper section of the receiving part 5. As such, the clamping element 7 can be inserted into the first end 5a of the receiving part 5 and moved downwardly or distally through the passage 51.

Figure 14:
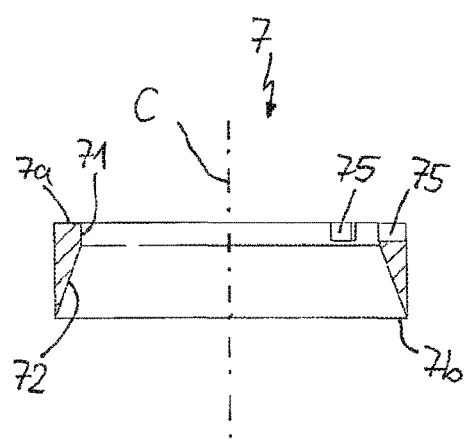
FIG. 14 shows a cross-sectional view of the clamping element of FIGS. 11 to 13, the cross-section taken along line CC-CC in FIG. 13.

As can be seen, for example, in FIGS. 2 and 14, an inner surface 71 of the clamping element adjacent to the first end 7a is cylindrical with an inner diameter slightly larger than an outer diameter of the first portion 61 of the pressure element 6. The cylindrical surface 71 of the ring-shaped clamping element 7 encompasses the outer cylindrical surface of the first portion 61 of the pressure element 6 in the mounted state. In addition, the clamping element 7 has a conically widening inner surface portion 72 between the cylindrical inner surface 71 and the second end 7b. The size of the conically widening inner surface portion 72 is such that the clamping element 7 can be mounted around the pressure element 6 with the inner surface portion 72 encompassing an upper region of the flexible second portion 63 of the pressure element 6. Thereby, the inner surface portion 72 contacts the first outer surface portion 65 of the flexible second portion 63 of the pressure element 6. By a downward movement of the clamping element 7 relative to the receiving part 5, the flexible second portion 63 of the pressure element 6 is compressed. Further, the inner surface portion 72 may have another shape that includes an increase in inner diameter towards the second end 7b.

Figure 11:
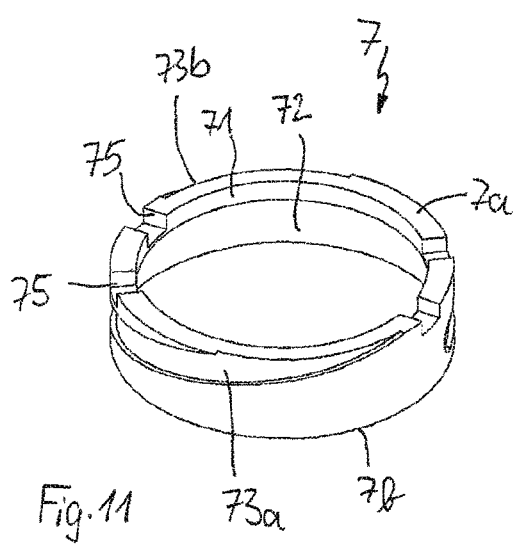
FIG. 11 shows a perspective view from above a clamping element of the coupling device according to the first embodiment of FIGS. 1 and 2.
Figure 12:
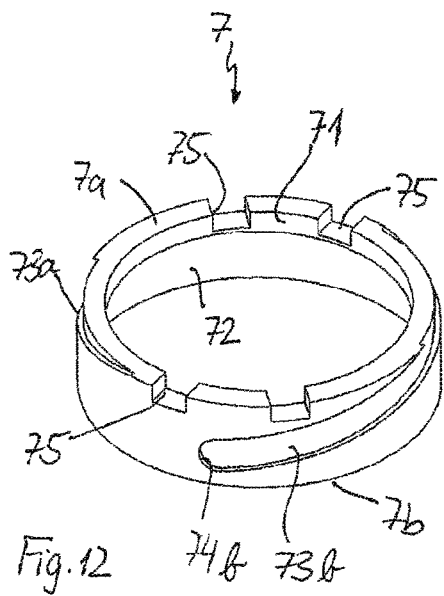
FIG. 12 shows another perspective view of the clamping element of FIG. 11.
Figure 13:
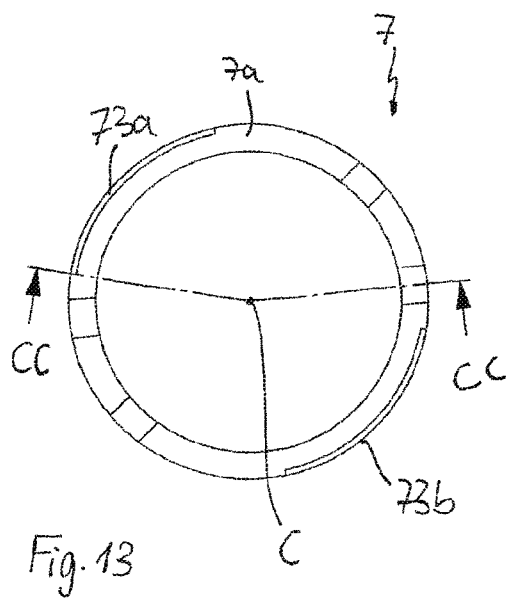
FIG. 13 shows a top view of the clamping element of FIGS. 11 and 12.

Referring in particular to FIGS. 11 and 12, two helical grooves 73a, 73b having the same pitch are provided on the outer surface of the clamping element 7. The helical grooves 73a, 73b are open towards the first end 7a and have closed ends 74a, 74b towards the second end 7b. The closed ends 74a, 74b may have rounded contours. A width of the grooves 73a, 73b is only slightly larger than the diameter of the pins 9a, 9b. In particular, the width of the grooves 73a, 73b in relation to the diameter of the pins 9a, 9b and the pitch may be such that a frictional force between the pins 9a, 9b and the grooves 73a, 73b results in a self-locking connection whereby the clamping element 7 can advance relative to the pins 9a, 9b only if a force is applied that exceeds the self-locking force. An inclination of the grooves 73a, 73b and a length of the grooves 73a, 73b between the open ends and the closed ends 74a, 74b is such that a desired advancement of the clamping element 7 in relation to an inserted pin 9a, 9b is possible. In the embodiment depicted in FIGS. 11 and 12, the grooves 73a, 73b each extend around the central axis C by more than around 90° and less than around 180°. However, any other inclination and length of the grooves 73a, 73b may be selected such that the clamping element 7 can be moved relative to the inserted pins 9a, 9b with a predetermined increment. The grooves 73a, 73b and the pins 9a, 9b form an advancement structure that permits the clamping element 7 to advance in the receiving part 5 by rotating the clamping element 7 around the axis of symmetry C. When the pressure element 6 and the clamping element 7 are inserted into the receiving part 5, the closed ends 74a, 74b of the helical grooves 73a, 73b prevent the clamping element 7 from escaping through the first end 5a. As such, the closed ends 74a, 74b form a securing structure.

As further depicted in FIGS. 11 to 14, the clamping element 7 includes a plurality of engagement portions or recesses 75 in the surface of the first end 7a that are configured to be engaged with a tool used for rotating the clamping element 7.

The parts of the bone anchoring device can be made of a bio-compatible material, such as a bio-compatible metal or a bio-compatible metal alloy, for example stainless steel, titanium, NiTi-alloys, such as Nitinol, magnesium or magnesium alloys or from a bio-compatible plastic material, such as, for example, polyether ether ketone (PEEK) or poly-l-lactide acid (PLLA). The parts of the bone anchoring device can be made of the same or of different materials.

Figure 15A:
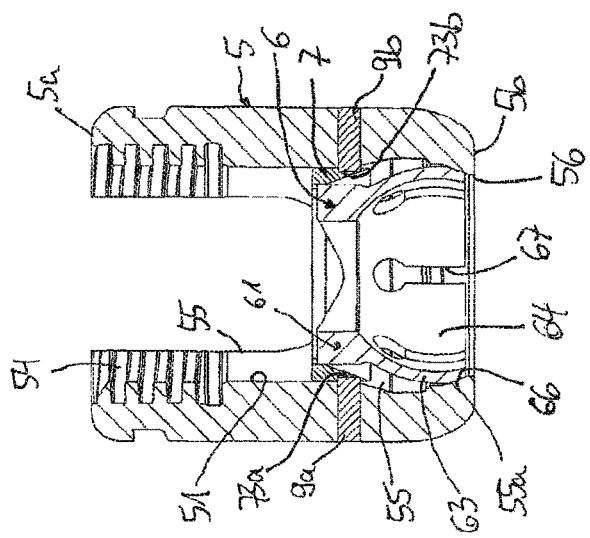
FIGS. 15a to 15c show cross sectional views of steps of placing the coupling device according to the first embodiment of FIGS. 1 to 14 onto a bone anchoring element.
Figure 15B:
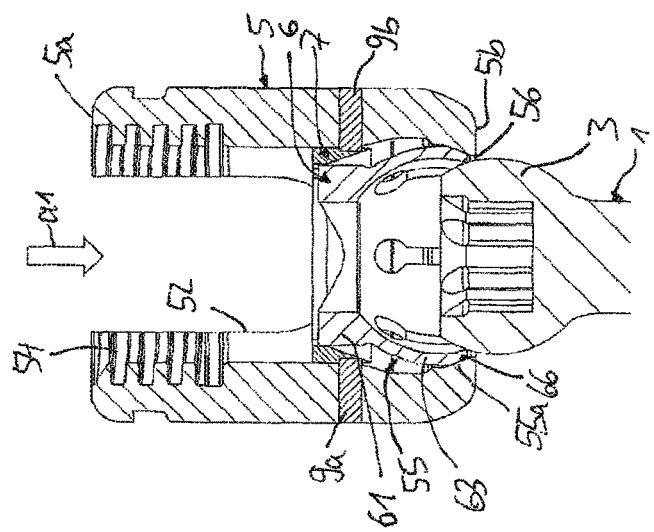
Figure 15C:
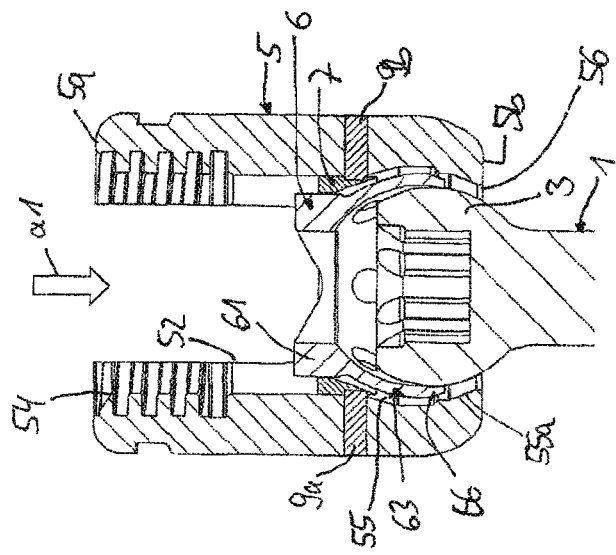

Referring to FIGS. 15a to 15c, steps of assembling the bone anchoring device of FIGS. 1 to 14 are explained. In FIG. 15a the pressure element 6 and the clamping element 7 are inserted into the receiving part 5. The pressure element 6 is in a position in which the second outer surface portion 66 of the pressure element abuts against the narrowing portion 55a of the receiving part 5. The pressure element 6 may be inserted from the lower opening 56 at the second end 5b or may be inserted through the first end 5a and moved downwardly or distally through the passage 51. The clamping element 7 is mounted such that the pins 9a, 9b rest in the closed end portion 74a, 74b of the helical grooves 73a, 73b, respectively, in an uppermost or first position of the clamping element 7. In this position, the clamping element 7 is arranged around the cylindrical first portion 61 of the pressure element 6 and does not contact the flexible second portion 63. Next, as depicted in FIG. 15b, the head 3 of the bone anchoring element is inserted into the pressure element 6 and the receiving part 5 through the lower opening 56 of the receiving part 5. In a first alternative, the bone anchoring device is assembled in-situ such that the bone anchoring element 1 has been already inserted into the bone and the coupling device, including the receiving part 5 with the pressure element 6 and the clamping element 7, is thereafter mounted onto the head 3 (arrow a1). In a second alternative, the bone anchoring device is assembled outside the human body and the head 3 is inserted manually into the receiving part 5 through the lower opening 56 before the bone anchoring element 1 is anchored to the bone.

Next, as depicted in FIG. 15c, the head 3 moves the pressure element 6 upward and the head 3 snaps into the hollow interior 64 of the flexible portion 63 of the pressure element 6. When the greatest diameter e of the head 3 passes the second end 6b of the pressure element and moves into the hollow interior 64, the flexible portion 63 can expand in the accommodation space 55 of the receiving part 5. During this step, the clamping element 7 stays in a fixed axial position and cannot be pushed upward or proximally as the clamping element 7 is held by the pins 9a, 9b.

Figure 15D:
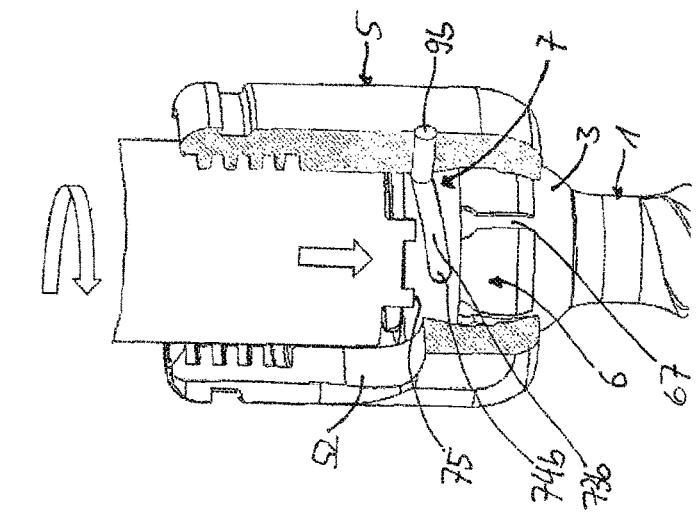
FIGS. 15d to 15f show cross-sectional views of steps of adjusting a clamping force onto an inserted head via the clamping element according to the first embodiment of FIGS. 1 to 14.
Figure 15E:
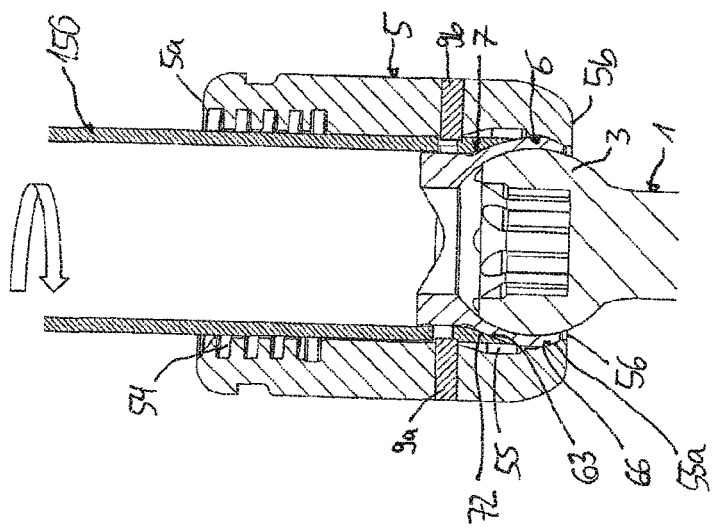
Figure 15F:
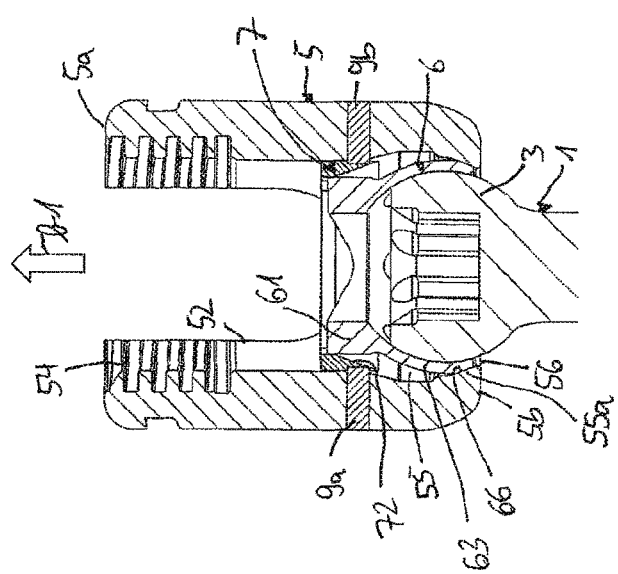
Figure 16:
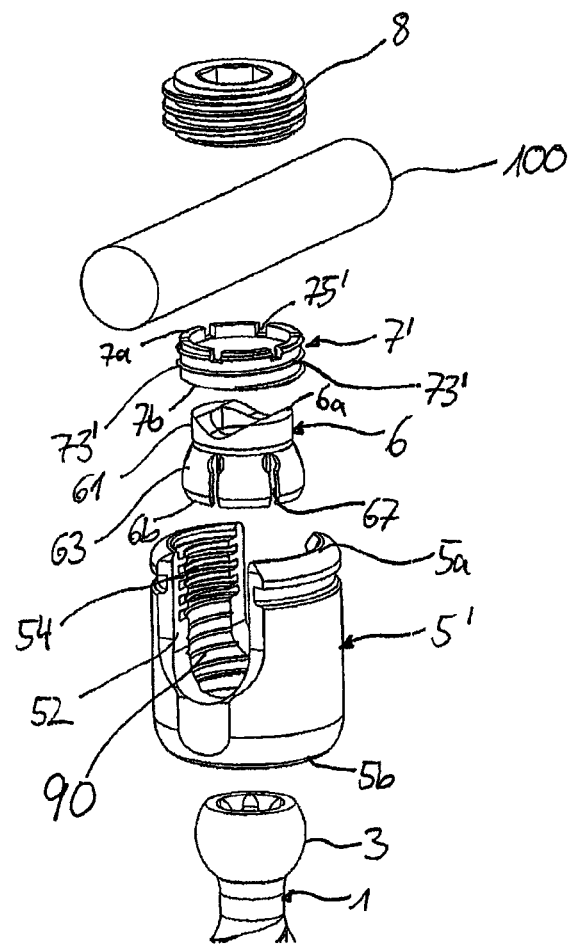
FIG. 16 shows an exploded perspective view of a second embodiment of a bone anchoring device with a second embodiment of a coupling device.

FIGS. 15d to 15f illustrate steps of achieving and adjusting a frictional clamping of the head 3. As depicted in FIG. 15d, when the head 3 has been fully inserted into the pressure element 6, the receiving part 5 may be pulled upwards (arrow b1), whereby the pressure element 6 together with the inserted head 3 is moved downward relative to the receiving part 5. The second outer surface portion 66 of the pressure element 6 passes the edge 55b protruding into the accommodation space 55 and enters the narrowing portion 55a whereby the second outer surface portion 66 is compressed and the head 3 is clamped by friction. In addition, the head 3 can no longer be removed through the lower opening 56 due to the force of the pressure element 6. This position is a pre-locking position of the pressure element 6.

In order to allow in-situ mounting of the receiving part 5 onto the head 3, a required insertion force for inserting the head 3 into the pressure element 6 should not be too high. However, if the insertion force is too low, resultant frictional clamping of the pressure element 6 onto the head 3 after insertion of the head 3 might not be strong enough for convenient handling.

To enhance frictional clamping of the head 3, the clamping element 7 is actuated in a next step using a tool 150 as shown in FIGS. 15e and 15f. The tool 150 may be formed as a tubular rod with engagement portions at a front or distal end that are arranged and sized to engage (e.g., fit in) the engagement portions 75 of the clamping element 7. The clamping element 7 is rotated by rotation of the tool 150 such that the pins 9a, 9b are guided in the helical grooves 73a, 73b. Thereby, the clamping element 7 advances downward until the inner surface portion 72 of the clamping element 7 contacts the first outer surface portion 65 of the pressure element 6. Further rotation of the tool 150 advances the clamping element 7 such that the clamping element 7 exerts a compression force onto the flexible second portion 63 of the pressure element 6 which increases the pressure of the pressure element 6 onto the inserted head 3. As a result thereof, the frictional force that holds the head 3 in a desired angular position relative to the receiving part 5 before final locking is increased. Due to the bayonet-like advancement structure of the clamping element 7, a stepless advancement of the clamping element 7 relative to the receiving part 5 is possible, which in turn provides a stepless adjustment of the compression force onto the head 3. FIG. 15f depicts a partial cross-sectional view which illustrates how the groove 73b has moved relative to the mounted pin 9b. With a self-locking connection between the groove 73b and the pin 9b, a desired position of the clamping element 7 in the receiving part 5 can be selected and maintained.

Finally, after alignment of the receiving part 5 of several bone anchoring devices, the rod 100 is inserted and the locking element 8 is tightened. Thereby, the pressure element 6 is further pressed against the narrowing portion 55a to lock the bone anchoring devices.

A second embodiment of the bone anchoring device and of the coupling device will be described with reference to FIGS. 16 to 23. Parts, portions, and elements that are identical or similar to those of the first embodiment are marked with the same reference numerals, and the descriptions therefore will not be repeated. The second embodiment differs from the first embodiment in the design of the clamping element and the advancement structure. All other parts are the same as in the first embodiment.

As depicted in FIGS. 16 to 20, the receiving part 5' includes an internal thread 90 that extends from the lower end of the internal thread 54 to an axial height of approximately slightly below the bottom of the U-shaped recess 52. The internal thread 90 may be separated from the internal thread 54 by the undercut 54a. A thread pitch of the internal thread 90 is substantially the same as a thread pitch of the internal thread 54 and a major diameter of the internal thread 90 is larger than a minor diameter of the internal thread 54. The shape of the internal thread 90 may be different from the shape of the internal thread 54. For example, the thread flanks of the internal thread 90 may have a triangular cross-section or any other cross-section. However, the dimensions of the threads of the internal thread 90 should be such that the clamping element 7 can be screwed through the upper portion of the passage 51 having the internal thread 54 and into the portion of the passage 51 having the internal thread 90. It should be noted, that the receiving part 5' does not need to have the pins 9a, 9b in this embodiment.

Figure 21:
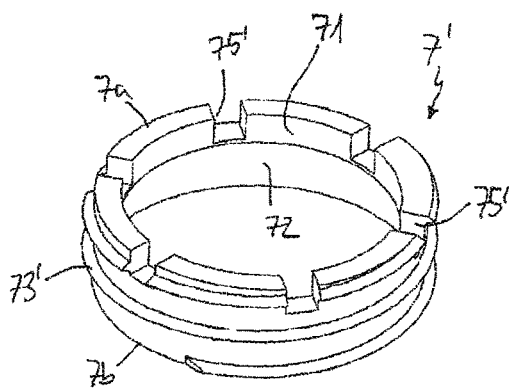
FIG. 21 shows a perspective view from above a clamping element of the coupling device according to the second embodiment of FIGS. 16 to 18.
Figure 22:
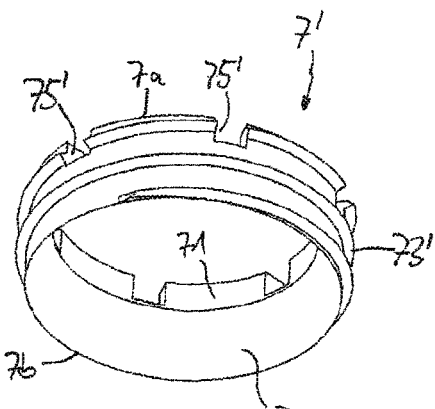
FIG. 22 shows a perspective view from below the clamping element of FIG. 21.
Figure 23:
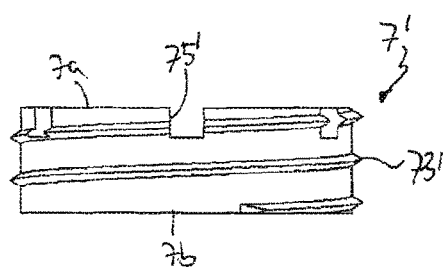
FIG. 23 shows a side view of the clamping element of FIGS. 21 and 22.
Figure 24:
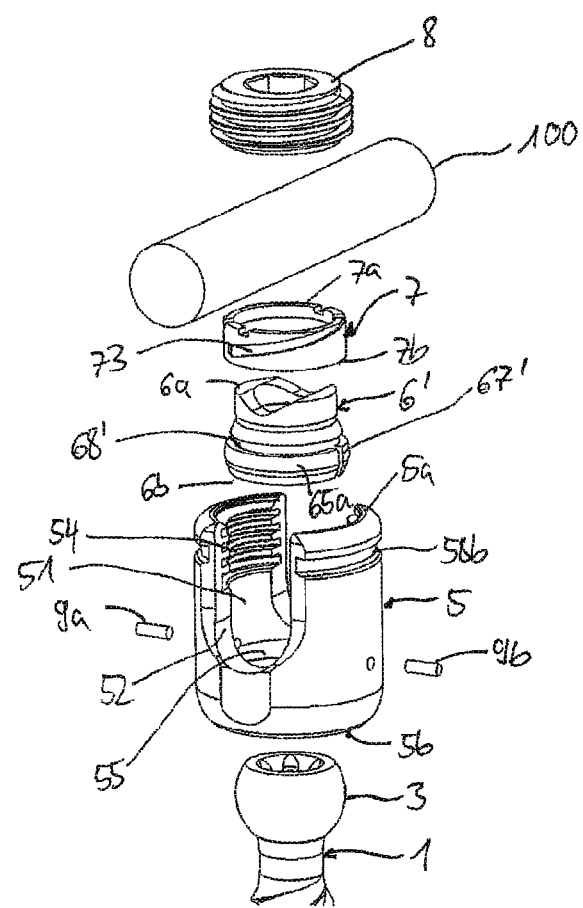
FIG. 24 shows an exploded perspective view of a third embodiment of a bone anchoring device with a third embodiment of a coupling device.

As shown in FIGS. 21 to 23, the clamping element 7' includes an external thread 73' provided on its outer cylindrical surface that is configured to cooperate with the internal thread 90 of the receiving part 5'. At the first end 7a, the clamping element 7' may have a plurality of engagement recesses 75'. In particular, the number of engagement recesses 75' may be greater than in the first embodiment. The advancement structure in the form of the cooperating threads 73', 90 provides a stepless advancement of the clamping element 7' relative to the receiving part 5'. The threaded connection between the clamping element 7' and the receiving part 5' acts as a securing structure that inhibits inadvertent movement of the clamping element 7' relative to the receiving part 5'.

In use, after the pressure element 6 has been inserted into the receiving part 5', the clamping element 7' is mounted to the receiving part 5' by screwing the clamping element 7' downward from the first end 5a. The clamping element 7' is moved downward to an axial position that still allows the pressure element 6 to move upward or proximally to insert the head 3. Screwing-in the clamping element 7' renders the assembly simple and safe, as jamming of the clamping element 7' in the passage 51 is prevented.

Figure 17:
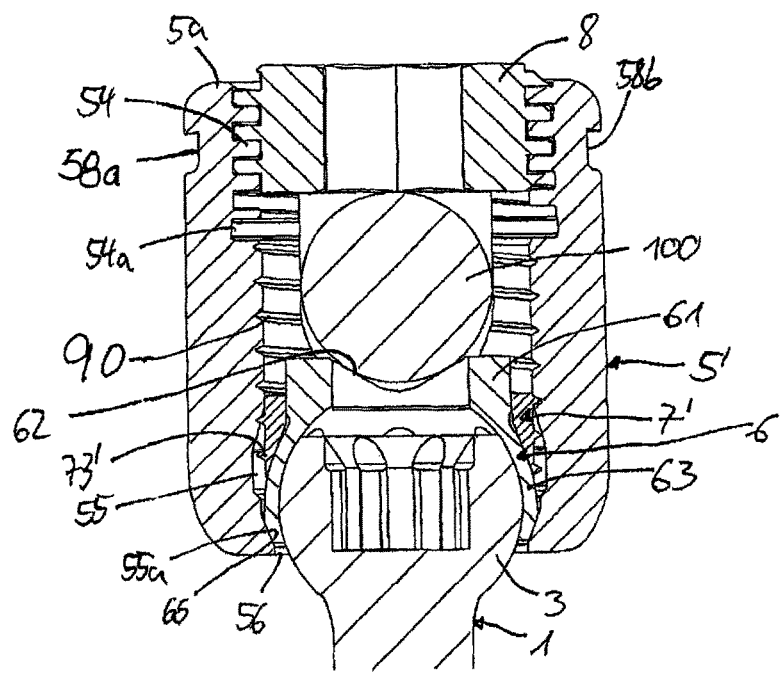
FIG. 17 shows a cross-sectional view of the bone anchoring device of FIG. 16, the cross-section taken in a plane perpendicular to a rod axis.
Figure 18:
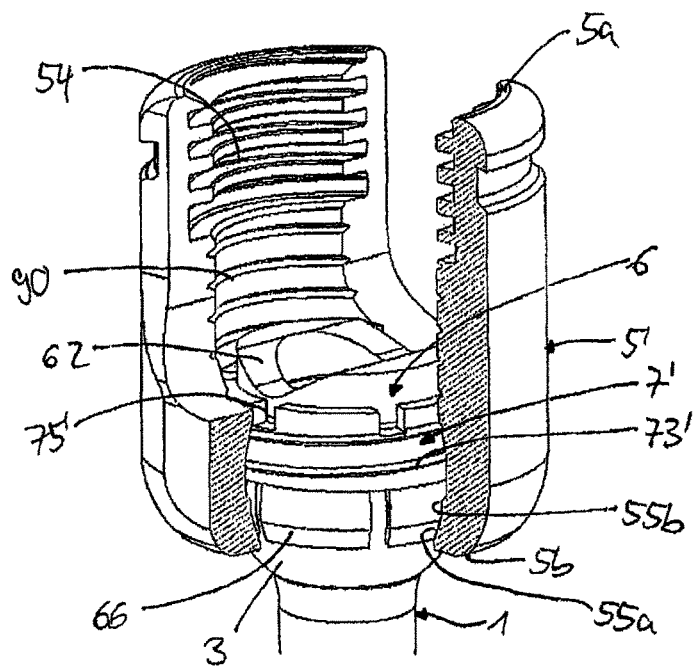
FIG. 18 shows a partial cross-sectional view of the bone anchoring device of FIGS. 16 and 17 without an inserted rod.
Figure 19:
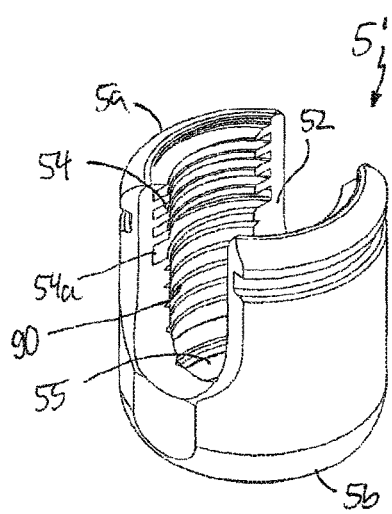
FIG. 19 shows a perspective view from above a receiving part of the coupling device according to the second embodiment of FIGS. 16 to 18.
Figure 20:
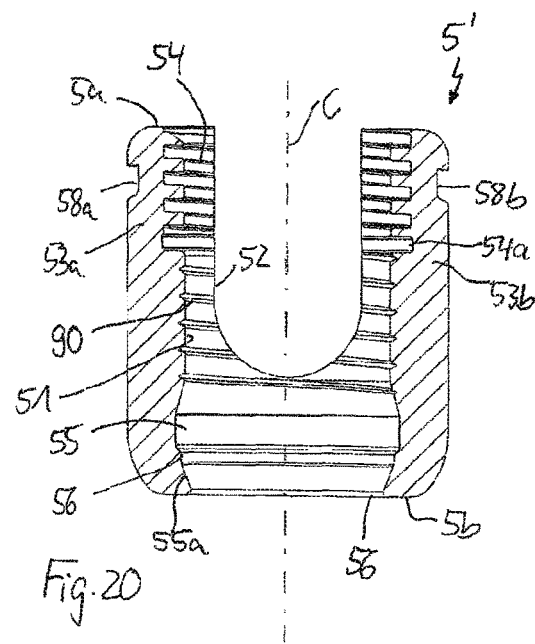
FIG. 20 shows a cross-sectional view of the receiving part of FIG. 19, the cross-section taken in a plane perpendicular to the rod axis.

When the head 3 has been inserted into the pressure element 6 and the pressure element 6 has reached the pre-locking position shown in FIG. 17, the clamping element 7' can be further screwed downward with a tool to exert a compression force onto the pressure element 6 to enhance the clamping force acting onto the head 3 by friction. After the rod 100 has been inserted and the locking element 8 has been tightened, the pressure element 6 is further pressed against the narrowing portion 55a to lock the bone anchoring device.

A third embodiment of the bone anchoring device will be described with reference to FIGS. 24 to 30. Parts, portions and elements of the third embodiment that are identical or similar to those of the first embodiment are marked with the same reference numerals and the descriptions thereof will not be repeated. The bone anchoring device differs from the first embodiment in the design of the coupling device and in particular in the design of the pressure element. The coupling device of the third embodiment includes the receiving part 5 and the clamping element 7 of the first embodiment and a modified pressure element 6'.

As shown, for example, in FIGS. 27-30, the flexible second portion 63' of the pressure element 6' includes one single vertical slit or recess 67' that is provided at an angle of substantially 90° in a circumferential direction relative to a longitudinal axis of the V-shaped rod support surface 62. The vertical recess 67' is open towards the second end 6b of the pressure element 6'. At a distance from the second end 6b, the vertical recess 67' opens into a horizontal recess 68' that extends in a circumferential direction from both sides from the vertical recess 67'. The horizontal recess 68' extends to ends that are spaced apart from each other. By means of the vertical recess 67' and the horizontal recess 68', a ring 65a is formed that is connected to the other portions of the pressure element 6'. The ring 65a is flexible and can be expanded and/or compressed. An upper portion of the pressure element 6' between the horizontal recess 68' and the cylindrical portion 61 has a substantially spherical outer surface that is slightly recessed with respect to the ring 65a.

In other words, the ring 65a has a slightly greater outer diameter forming a circumferential edge 65b.

Figure 25:
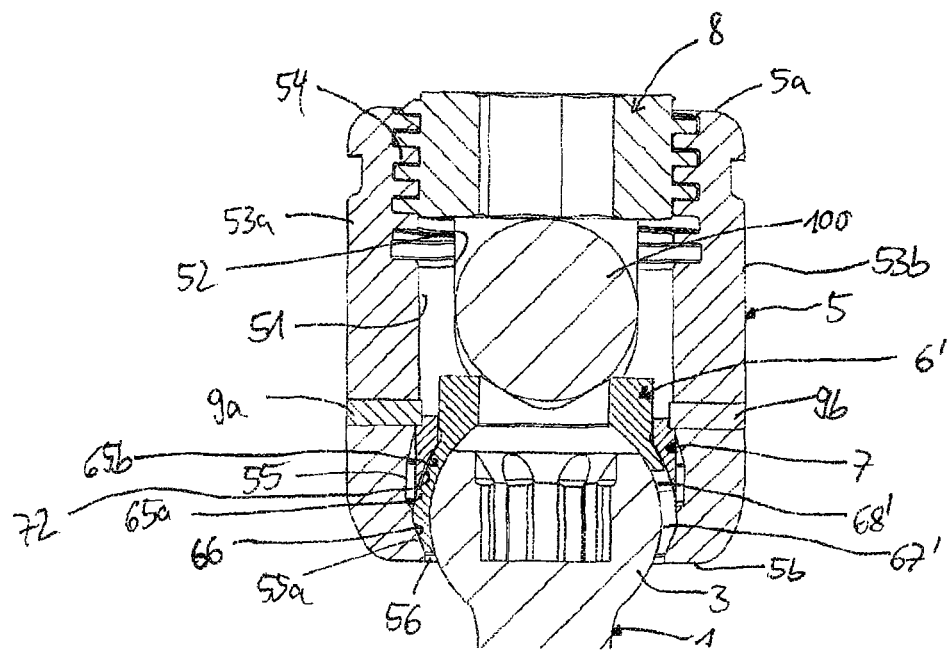
FIG. 25 shows a cross-sectional view of the bone anchoring device of FIG. 24, the cross-section taken in a plane perpendicular to the rod axis.
Figure 26:
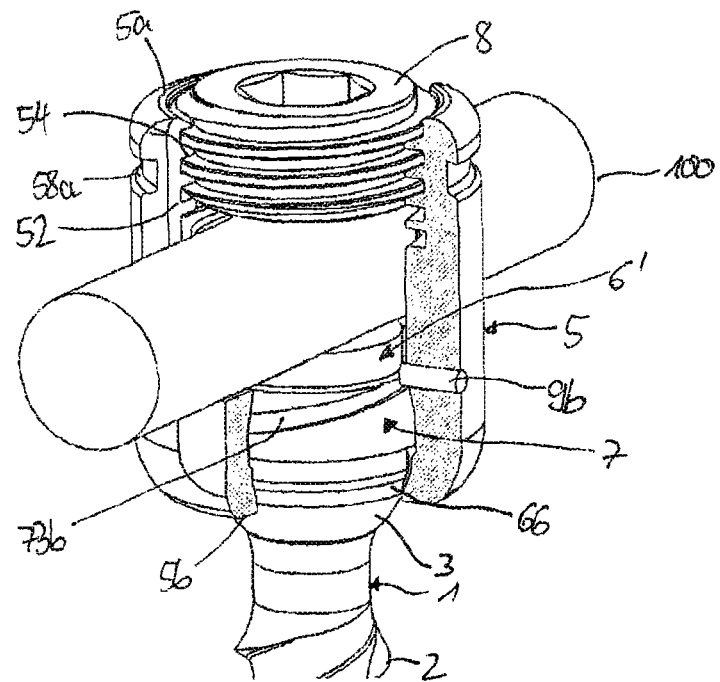
FIG. 26 shows a partial cross-sectional view of the bone anchoring device of FIGS. 24 and 25.
Figure 31:
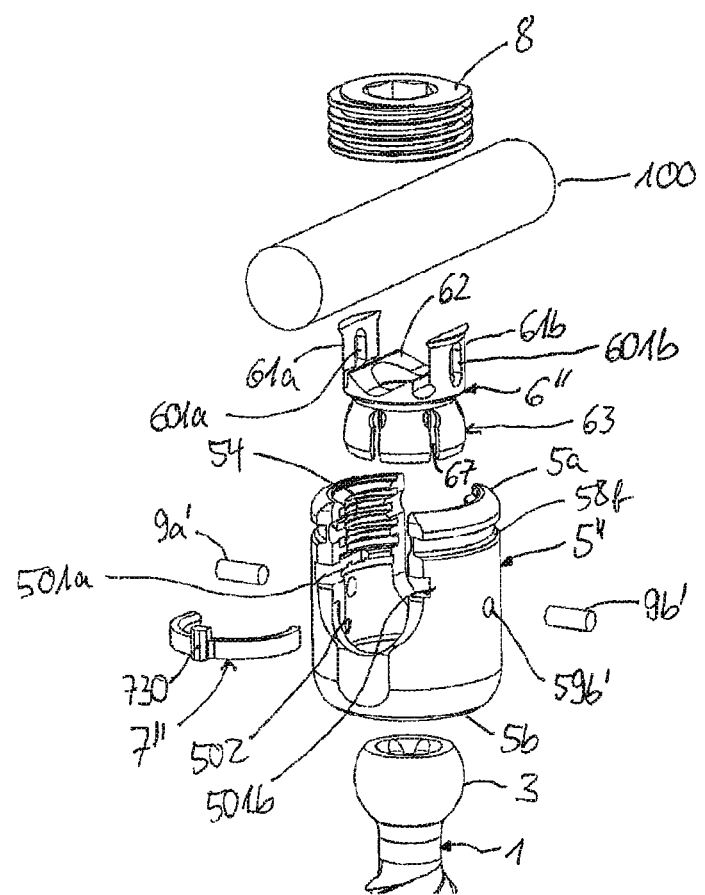
FIG. 31 shows an exploded perspective view of a fourth embodiment of a bone anchoring device with a fourth embodiment of a coupling device.

As depicted in FIGS. 25 and 26, in the assembled state when the clamping element 7 has been moved downward to contact the pressure element 6', the clamping element 7 presses the pressure element 6' with the inner surface portion 72 onto the edge of the ring 65a that has the slightly greater diameter.

The use of the bone anchoring device according to the third embodiment is analogous to the use of the bone anchoring devices according to the previous embodiments. However, the horizontal slit 68' in connection with the vertical slit 67' renders the second portion 63' of the pressure element 6' more flexible than the previous embodiments. Therefore, the amount of insertion force required to insert the head 3 into the pressure element 6' may be decreased relative to previous embodiments. In turn, the amount of frictional force needed to hold the inserted head 3 in the pressure element 6' and the receiving part 5 may be smaller. By means of the clamping element 7, the frictional force can be increased relative to previous embodiments.

A fourth embodiment of the bone anchoring device will be explained with reference to FIGS. 31 to 45. Parts, portions and elements that are identical or similar to the parts, portions and elements of the previous embodiments are indicated with the same reference numerals and the descriptions thereof will not be repeated. The bone anchoring device of the fourth embodiment differs from the previous embodiments in the structure of the receiving part, the pressure element and the clamping element.

Referring to FIGS. 31 to 37, the receiving part 5" is adapted to accommodate the clamping element 7". The receiving part 5" includes opposite horizontal slits 501a, 501b on each leg 53a, 53b. The opposite horizontal slits 501a, 501b are located at one side of the U-shaped recess 52. The slits 501a, 501b extend substantially perpendicular to the central axis C and are open towards the outer surface of the legs 53a, 53b. At their outer region, the slits 501a, 501b may have a substantially square or rectangular cross-section with a size adapted to accommodate at least a portion of the clamping element 7" therein. The slits 501a, 501b are located at an axial position that is approximately at the lower end of the internal thread 54, which allows mounting the clamping element 7" to the receiving part 5" from the side through the U-shaped recess 52.

At the side of the slits 501a, 501b, a substantially vertically extending shallow recess 502 is provided that extends from the bottom of the substantially U-shaped recess 52 towards the second end 5b. A width of the shallow vertical recess 502 in a circumferential direction is slightly larger than half of the distance between the legs 53a, 53b, as can be seen in particular in FIG. 36. The shallow recess 502 serves as a space for a portion of the clamping element 7" to permit the clamping element 7" to rotate between a first position and a second position and to limit the movement of the clamping element 7" between these positions. Moreover, two opposite bores 59a', 59b' are provided at approximately the center of the legs 53a, 53b and at an axial position slightly below the axial position of the horizontal slits 501a, 501b. The bores 59a', 59b' are configured to accommodate pins 9a', 9b', respectively therein. The pins 9a', 9b' are configured to engage the pressure element 6" as explained below.

Turning now to FIGS. 38 to 41, the pressure element 6" differs from the pressure element of the first and second embodiments by the shape of the upper portion adjacent to the flexible second portion 63. The flexible second portion 63 is identical to the flexible second portion 63 of the first embodiment. The cylindrical first portion 61' has an outer diameter that is greater than an outer diameter of the flexible second portion 63 in the upper region, hence, the flexible second portion 63 is recessed with respect to the first portion 61'. The first portion 61' includes two opposite upstanding legs 61a, 61b. Grooves 62a, 62b respectively separate the upstanding legs 61a, 61b from an inner portion having the rod supporting surface 62. The grooves 62a, 62b may have a widened bottom to render the legs 61a, 61b slightly flexible to aid with insertion. The grooves 62a, 62b extend substantially parallel to the longitudinal axis of the rod support surface 62. An inner surface of the legs 61a, 61b is substantially flat. At an upper end of the legs 61a, 61b, the legs 61a, 61b each include collar portions 600a, 600b. The collar portions 600a, 600b are shaped to fit in a corresponding cutout in the receiving part 5" in the region of the horizontal slits 501a, 501b, as shown in particular in FIG. 33. The legs 61a, 61b each include an elongate through-hole 601a, 601b, the longitudinal axes of which are substantially parallel to the central axis C. The through-holes 601a, 601b are configured to receive the pins 9a', 9b', respectively. When the pins 9a', 9b' engage the through-holes 601a, 601b, the pressure element 6" is restricted to move only a predetermined distance in the axial direction and is limited by the abutment of the pins 9a', 9b' against the respective ends of the through-holes 601a, 601b in the axial direction.

Figure 32:
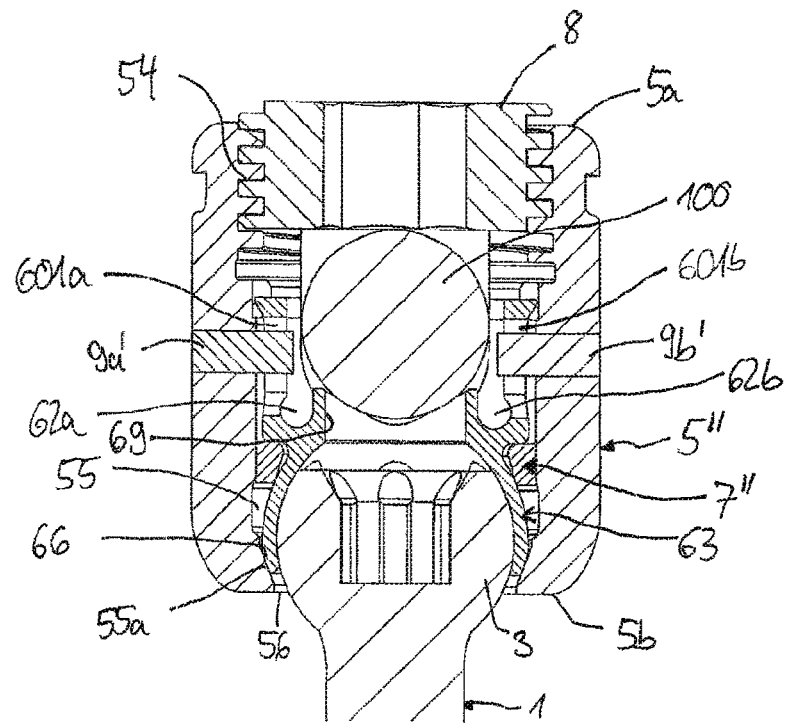
FIG. 32 shows a cross-sectional view of the bone anchoring device of FIG. 31, the cross-section taken in a plane perpendicular to a rod axis.
Figure 33:
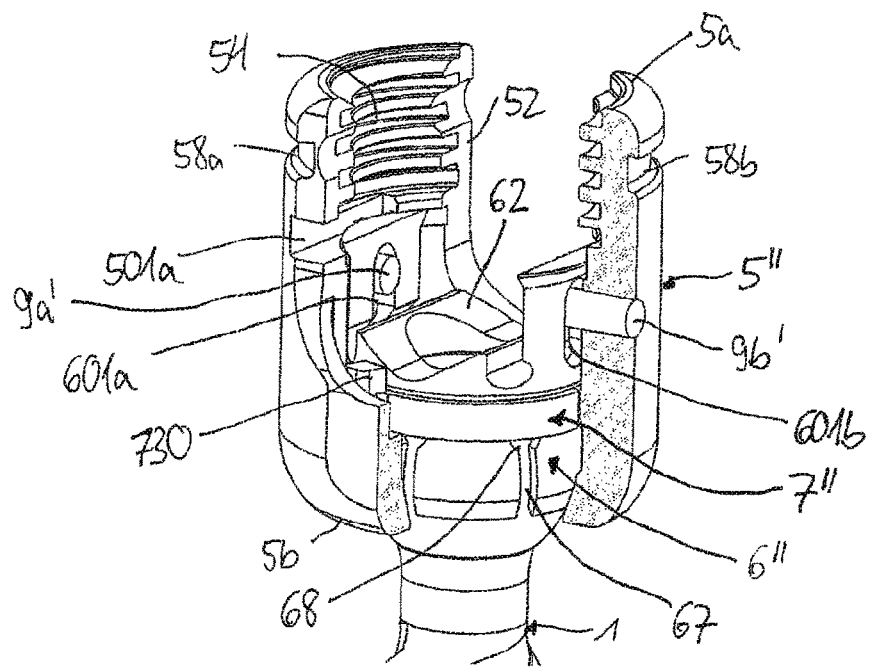
FIG. 33 shows a partial cross-sectional view of the bone anchoring device of FIGS. 31 and 32 without an inserted rod.
Figure 38:
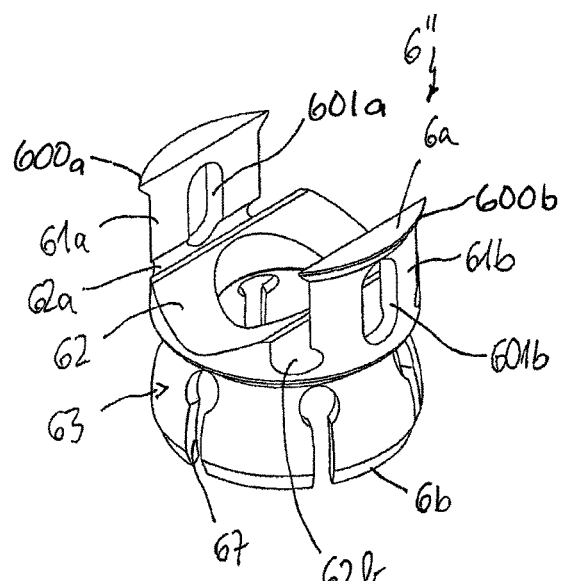
FIG. 38 shows a perspective view from above a pressure element of the fourth embodiment of FIGS. 31 to 33.
Figure 39:
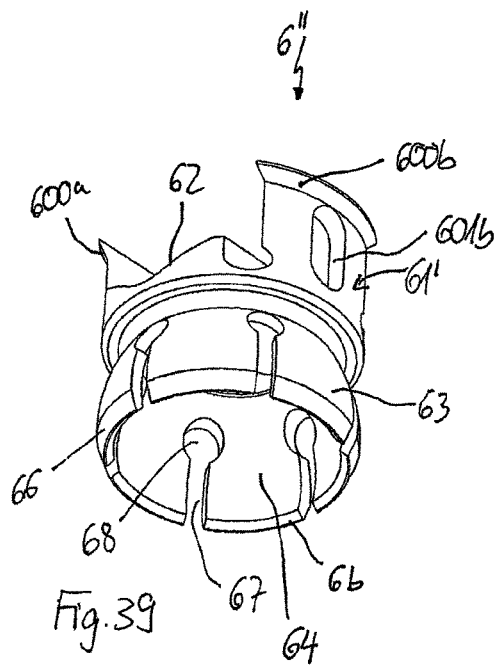
FIG. 39 shows a perspective view from below the pressure element of FIG. 38.
Figure 40:
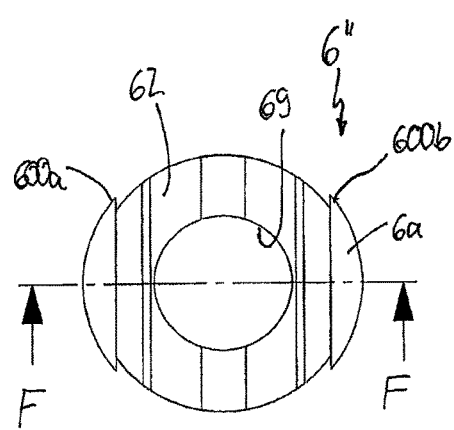
FIG. 40 shows a top view of the pressure element of FIGS. 38 and 39.
Figure 41:
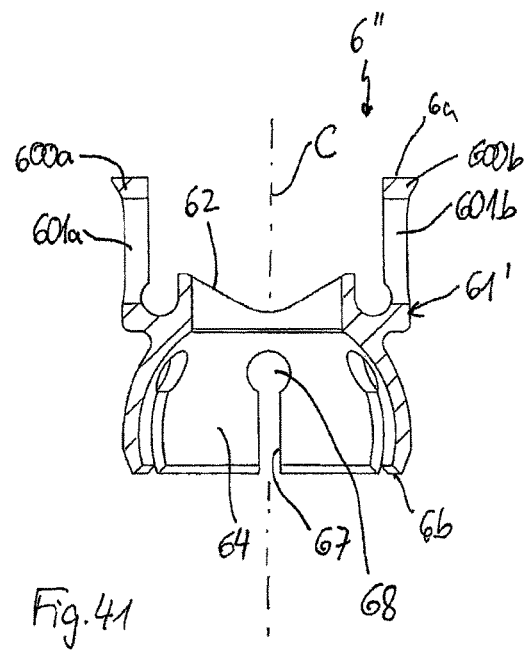
FIG. 41 shows a cross-sectional view of the pressure element of FIGS. 38 to 40, the cross-section taken along line F-F in FIG. 40.
Figure 42:
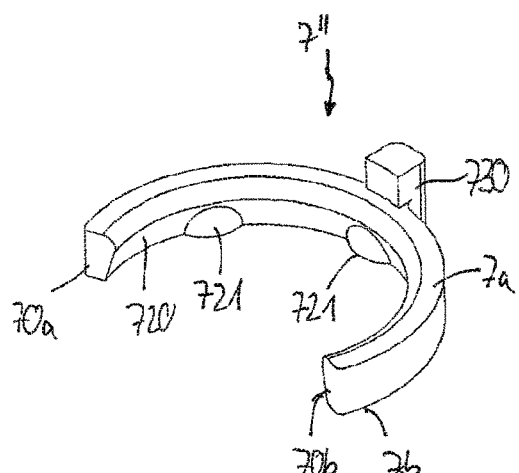
FIG. 42 shows a perspective view from above a clamping element of the fourth embodiment of FIGS. 31 to 33.
Figure 43:
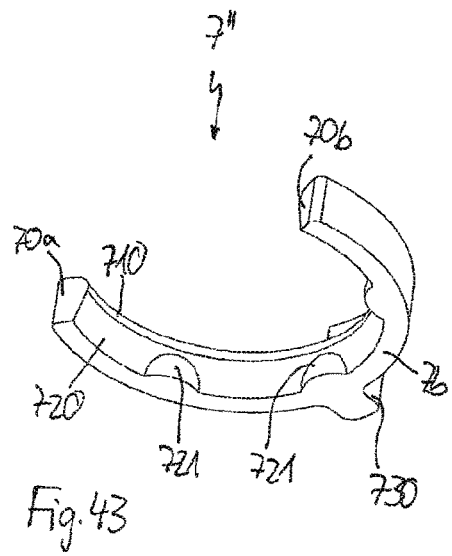
FIG. 43 shows a perspective view from below the clamping element of FIG. 42.
Figure 44:
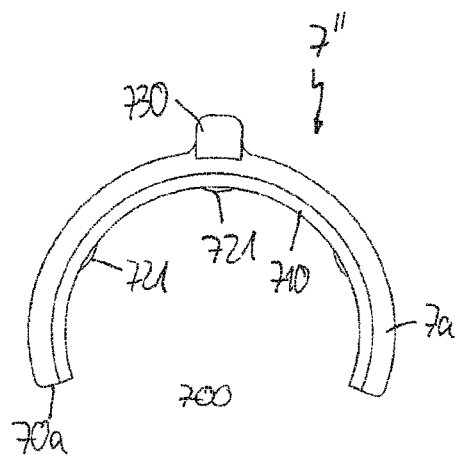
FIG. 44 shows a top view of the clamping element of FIGS. 42 and 43.
Figure 45:
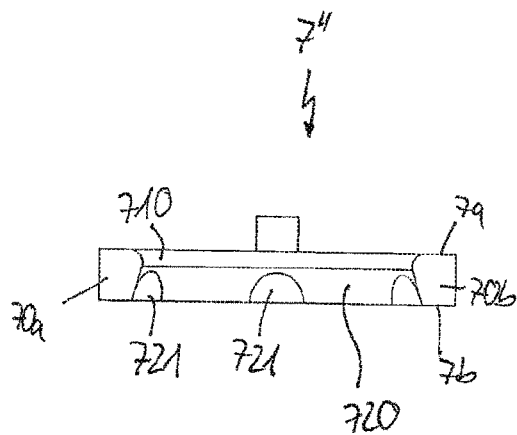
FIG. 45 shows a side view of the clamping element of FIGS. 42 to 44.

The clamping element 7" of the fourth embodiment will be explained with reference to FIGS. 31 to 33 and 42 to 45. The clamping element 7" is shaped as an open ring having free ends 70a, 70b and a slot 700 therebetween such that the clamping element 7" can act as a snap ring. More in detail, the clamping element 7" extends slightly more than 180° in a circumferential direction around the central axis C. The slot 700 may be smaller or may be larger than as shown. Further, the clamping element 7" has a substantially cylindrically shaped outer wall with an axial length such that the clamping element 7" fits approximately into a recessed region between the first portion 61' and the second portion 63 of the pressure element 6", as shown in FIG. 32. As further depicted in FIG. 32, the clamping element 7" has a substantially conically widening inner surface portion 720 that is adapted to extend around the upper section of the flexible second portion 63 of the pressure element 6". Between the widening inner surface portion 720 and the first end 7a of the clamping element 7", there may be a portion 710 that can be rounded to avoid jamming of the clamping element 7" during mounting. A plurality of rounded protrusions 721 are provided in the widening inner surface portion 720 that are configured to engage the widened end portions 68 of the slits 67 of the flexible portion 63 of the pressure element 6". It shall be noted that a modification of the design of the pressure element 6" and the clamping element 7" may be conceivable. Instead of the widened portions 68 of the slit 67 in the pressure element 6" and the rounded protrusions 721 on the inner surface of the clamping element 7", protrusions could be present at the end of the slits 67 of the pressure element 6" and corresponding dimples could be present in the inner surface of the clamping element 7".

At approximately the center of the clamping element 7" in a circumferential direction, a protrusion 730, with a substantially rectangular cross-section, is provided at the outer surface of the clamping element 7" opposite to the protrusions 721. In the axial direction, the protrusion 730 extends above the first end 7a. The protrusion 730 serves for engagement with a tool for moving the clamping element 7" relative to the pressure element 6".

Mounting of the pressure element 6" and the clamping element 7" into the receiving part 5" according to the fourth embodiment will be explained with reference to FIGS. 46a to 46d. In a first step, the pressure element 6" is inserted into the receiving part 5" from the first end 5a. Upon insertion into the receiving part 5", the legs 61a, 61b may be slightly flexed towards each other such that the pressure element 6" can be maintained at a desired axial position. When the region of the pressure element 6" between the cylindrical first portion 61' and the flexible second portion 63 is located at an axial height of approximately the horizontal slits 501a, 501b, the clamping element 7" is inserted into the slits 501a, 501b of the receiving part 5" until the clamping element 7" extends around the pressure element 6" just beneath the cylindrical first portion 61'. In this configuration, the protrusion 730 of the clamping element 7" is aligned with the center of the substantially U-shaped recess of the receiving part 5", and the rod support surface 62 of the pressure element 6" is also aligned with the U-shaped recess 52 of the receiving part 5". Further, one of the slits 67 is located at a circumferential position corresponding to the center of the rod support surface 62 of the pressure element 6". A corresponding protrusion 721 at the widening inner surface portion 720 of the clamping element 7" can engage the widened portion 68 of the slit 67 as depicted in FIG. 46c. Thereafter, as shown in FIG. 46d, the pressure element 6" and the clamping element 7" are moved downward together as indicated by the arrow a1. Thereby, the elongate through-holes 601a, 601b overlap with the bores 59a', 59b' such that the pins 9a', 9b' can be inserted into the bores 59a', 59b' and extend into the through-holes 601a, 601b.

Use of the bone anchoring device of the fourth embodiment will be explained with reference to FIGS. 46e to 46h. First, as depicted in FIG. 46e, the receiving part 5" with the mounted pressure element 6" and clamping element 7" is placed onto the head 3 of the bone anchoring element 1. This may be performed in-situ after the bone anchoring element 1 has been already inserted into the bone. As with the previous embodiments, the pressure element 6" snaps onto the head 3 such that the head 3 is accommodated in the pressure element 6" and in the accommodation space 55 of the receiving part 5" as shown in FIG. 46f. Thereafter, as illustrated in FIG. 46g, the receiving part 5" is pulled upward or proximally according to the arrow b1. The pins 9a', 9b' respectively move upward in the elongate through-holes 601a, 601b of the pressure element 6". The protrusion 730 of the clamping element 7" moves at least partially into the shallow recess 502 of the receiving part 5". In this position, the pressure element 6" has reached the pre-locking position where it is no longer possible to remove the head 3 through the lower opening 56.

Thereafter, as shown in FIG. 46h, the clamping element 7" is rotated in the clockwise direction around the central axis C (arrow c1). The clamping element 7" may be rotated using a tool that engages the protrusion 730 of the clamping element 7". Thereby, the rounded protrusions 721 of the clamping element 7" move out of the widening portions 68 of the pressure element 6" and press against the flexible second portion 63 of the pressure element 6". The compression of the rounded protrusions 721 against the flexible second portion 63 of the pressure element 6" increases the clamping force acting on the head 3. The rotational movement of the clamping element 7" relative to the receiving part 5" is limited by the abutment of the protrusion 730 against the sidewall of the shallow recess 502. Moreover, the pins 9a', 9b' prevent the pressure element 6" from escaping out of the receiving part 5".

The steps of inserting the rod 100 and the locking element 8, and tightening the locking element 8 to lock the bone anchoring device are identical to the previous embodiments.

A fifth embodiment of the polyaxial bone anchoring device and the coupling device will be described with reference to FIGS. 47a to 50. The bone anchoring element 1 of the fifth embodiment is identical to the previous embodiments. The receiving part 5", the clamping element 7", and the pressure element 6" are manufactured as a monolithic piece and are separated after manufacturing. The pressure element 6" of the fifth embodiment has a shape similar to the pressure element in the first embodiment. The clamping element 7" of the fifth embodiment is similar to the clamping element of the first and second embodiments, however, instead of the two grooves 73a, 73b, the clamping element 7" has two helical projections 7000a, 7000b on its outer surface. The helical projections 7000a, 7000b are configured to engage corresponding helical grooves 9000a, 9000b in the receiving part 5". As shown in more detail in FIGS. 47a and 47b, the clamping element 7" is monolithically connected to the pressure element 6" at predetermined breaking points P. The predetermined breaking points P are configured to break such that the clamping element 7" and the pressure element 6" become separated. The predetermined breaking points P have such a size that they break when a tool engages the engagement portions 75 of the clamping element 7" and rotates the clamping element 7". Similarly, the clamping element 7" is monolithically connected to the receiving part 5" at predetermined breaking points Q as shown in FIGS. 48 and 50. The size of the breaking points Q is such that the connection between the receiving part 5" and the clamping element 7" breaks at the predetermined breaking points Q by rotation of the clamping element 7" with a tool.

The receiving part 5", the pressure element 6", and the clamping element 7" may be separated before mounting the coupling device to a bone anchoring element 1. In particular, the pressure element 6" and the clamping element 7" may be manufactured such that the position of the pressure element 6" is an inserting position for inserting the head 3. The separation can take place during mounting of the receiving part 5" onto the head 3 of the bone anchoring element 1 in-situ.

A method for manufacturing the coupling device according to the fifth embodiment may be performed by an additive manufacturing method, such as selective laser sintering, selective laser melting, electron beam-sintering, and/or electron beam-melting.

Modifications of the above described embodiments are possible. For the bone anchoring element all kinds of bone anchors can be used, such as screws, nails with or without barbs, cannulated bone anchors, two-part bone anchors where head and shaft are separate parts that can be assembled, and other bone anchoring elements. The head of the bone anchoring element may have a design that allows the bone anchoring element with a pressure element adapted thereto to be pivoted only in a single plane. For example, the head may have at least one flat surface portion extending substantially parallel to the shaft axis and the pressure element may have a cooperating portion to limit the pivoting to a single plane. Any design for providing an enlarged pivot angle may be used also.

For the locking element all kinds of locking devices can be used, such as bayonet-type locking devices, two-part locking devices that allow clamping the rod and the head independently with two locking elements, outer locking nuts, and the like.

While some of the embodiments include two pins, it shall be understood that one pin is sufficient.

The features of the above described embodiments can be combined among each other to provide a variety of still further embodiments.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

The invention claimed is:

1. A coupling device for coupling a rod to a bone anchoring element, the coupling device comprising:
   a receiving part having a first end, a second end below the first end, a central axis extending through the first end and the second end, a channel at the first end for receiving the rod, and a portion at the second end that is configured to facilitate a pivotable connection between the receiving part and the bone anchoring element;
   a pressure element movable relative to the receiving part and configured to pivot together with the receiving part relative to a connected bone anchoring element and to exert pressure on the connected bone anchoring element that is directed towards the first end of the receiving part to lock an angular position of the connected bone anchoring element relative to the pressure element and the receiving part, and
   a clamping element separable from the pressure element that is configured to be held by the receiving part at a first position and to be held by the receiving part at a second position different from the first position, wherein at the second position the clamping element extends to an axial position that is below a bottom of the channel, and wherein a clamping force exerted on the connected bone anchoring element is greater when the clamping element is at the second position than when the clamping element is at the first position.

2. The coupling device of claim 1, wherein the pressure element comprises an expandable portion configured to receive a head of the bone anchoring element.

3. The coupling device of claim 2, wherein the expandable portion of the pressure element has a cap-like shape and is configured to surround the head.

4. The coupling device of claim 2, wherein the pressure element is configured to extend beyond a largest diameter of the head towards the second end of the receiving part, and wherein the clamping element is provided at an axial position above the largest diameter of the head in a direction of the first end.

5. The coupling device of claim 1, wherein the clamping element comprises an engagement portion for engagement with a tool to move the clamping element from the first position to the second position to adjust the clamping force.

6. The coupling device of claim 1, wherein the first position and the second position are at different axial positions relative to the receiving part.

7. The coupling device of claim 1, wherein the clamping element comprises protrusions or recesses configured to cooperate with recesses or protrusions on other parts of the coupling device to adjust the clamping force.

8. The coupling device of claim 1, wherein the pressure element and the clamping element are manufactured as a monolithic piece, and are configured to be separated from each other at a predetermined breaking point.

9. The coupling device of claim 1, wherein the clamping element is configured to extend at least partially around the pressure element.

10. The coupling device of claim 1, wherein the receiving part defines an accommodation space for accommodating a head of the bone anchoring element and an opening at the second end for inserting the head into the accommodation space.

11. The coupling device of claim 1, wherein the receiving part defines a coaxial bore extending from the first end to the second end, and wherein the pressure element and the clamping element are insertable and positionable in the coaxial bore.

12. The coupling device of claim 1, wherein the clamping element has a different rotational orientation relative to the receiving part in the second position compared to the first position.

13. A bone anchoring device for coupling a rod to a bone, the bone anchoring device comprising:
a bone anchoring element having a shank for anchoring to the bone and a spherical surface having at least a portion directed towards the shank;
a receiving part having a first end, a second end, a central axis extending through the first end and the second end, a channel at the first end for receiving the rod, and a portion at the second end that is configured to facilitate a pivotable connection between the receiving part and the bone anchoring element when the bone anchoring element is attached to the receiving part from the second end; and
a clamping element positionable between the receiving part and the bone anchoring element, the clamping element comprising at least one engagement portion for engagement with a tool,
wherein when the bone anchoring element is connected to the receiving part, the clamping element is configured to be held directly by the receiving part at a first position, is adjustable from the first position to a second position different from the first position using the at least one engagement portion, is configured to be held directly by the receiving part at the second position, and is adjustable from the second position back towards the first position using the at least one engagement portion, and wherein a clamping force exerted on the bone anchoring element is greater when the clamping element is at the second position than when the clamping element is at the first position.

14. The bone anchoring device of claim 13, wherein the receiving part defines a coaxial bore extending from the first end to the second end, and wherein the clamping element is insertable and positionable in the coaxial bore.

15. The bone anchoring device of claim 13, wherein the bone anchoring element further comprises a head, and wherein the receiving part defines an accommodation space for accommodating the head and an opening at the second end for inserting the head into the accommodation space.

16. The bone anchoring device of claim 15, further comprising a pressure element configured to hold the head in the receiving part, wherein the clamping element is configured to extend at least partially around the pressure element.

17. The bone anchoring device of claim 13, wherein the clamping element comprises protrusions or recesses configured to cooperate with recesses or protrusions on other parts of the bone anchoring device to adjust the clamping force.

18. The bone anchoring device of claim 13, wherein the first position and the second position are at different axial positions relative to the receiving part.

19. The bone anchoring device of claim 13, wherein the clamping element has a different rotational orientation relative to the receiving part in the second position compared to the first position.

20. A method for coupling a rod to a bone with a bone anchoring device, the bone anchoring device comprising: a bone anchoring element having a shank for anchoring to the bone and a spherical surface having at least a portion directed towards the shank, a receiving part having a first end, a second end, a central axis extending through the first end and the second end, a channel at the first end for receiving the rod, and a portion at the second end that is configured to facilitate a pivotable connection between the receiving part and the bone anchoring element when the bone anchoring element is attached to the receiving part from the second end, a clamping element positionable between the receiving part and the bone anchoring element, the clamping element comprising at least one engagement portion for engagement with a tool, and a locking element, wherein when the bone anchoring element is connected to the receiving part, the clamping element is configured to be held directly by the receiving part at a first position, is adjustable from the first position to a second position different from the first position using the at least one engagement portion, is configured to be held directly by the receiving part at the second position, and is adjustable from the second position back towards the first position using the at least one engagement portion, the method comprising:
anchoring the bone anchoring element to a bone;
adjusting an angular position of the receiving part relative to the bone anchoring element;
moving the clamping element from the first position to the second position to increase a clamping force exerted on the bone anchoring element;
inserting a rod into the channel of the receiving part; and
engaging the locking element with the receiving part to lock the rod and the bone anchoring element relative to the receiving part.

* * * * *

UNITED STATES PATENT AND TRADEMARK OFFICE
CERTIFICATE OF CORRECTION

PATENT NO. : 10,271,877 B2
APPLICATION NO. : 15/818278
DATED : April 30, 2019
INVENTOR(S) : Lutz Biedermann et al.

It is certified that error appears in the above-identified patent and that said Letters Patent is hereby corrected as shown below:

In the Specification

| | |
|---|---|
| Column 15, Line 8 | delete "5"," and insert -- 5'", -- |
| Column 15, Line 9 | delete "7"," and insert -- 7'", -- |
| Column 15, Line 9 | delete "6"" and insert -- 6'" -- |
| Column 15, Line 11 | delete "6"" and insert -- 6'" -- |
| Column 15, Line 13 | delete "7"" and insert -- 7'" -- |
| Column 15, Line 16 | delete "7"" and insert -- 7'" -- |
| Column 15, Line 19 | delete "5"." and insert -- 5'". -- |
| Column 15, Line 20 | delete "7"" and insert -- 7'" -- |
| Column 15, Line 21 | delete "6"" and insert -- 6'" -- |
| Column 15, Line 23 | delete "7"" and insert -- 7'" -- |
| Column 15, Line 24 | delete "6"" and insert -- 6'" -- |
| Column 15, Line 27 | delete "7"" and insert -- 7'" -- |
| Column 15, Line 27 | delete "7"." and insert -- 7'". -- |

Signed and Sealed this
Eighteenth Day of February, 2020

Andrei Iancu
*Director of the United States Patent and Trademark Office*

CERTIFICATE OF CORRECTION (continued)
U.S. Pat. No. 10,271,877 B2

Column 15, Line 28     delete "7''" and insert -- 7''' --
Column 15, Line 29     delete "5''" and insert -- 5''' --
Column 15, Line 32     delete "5''" and insert -- 5''' --
Column 15, Line 32     delete "7''" and insert -- 7''' --
Column 15, Line 34     delete "7''" and insert -- 7''' --
Column 15, Line 35     delete "5''," and insert -- 5''', --
Column 15, Line 35     delete "6''," and insert -- 6''', --
Column 15, Line 36     delete "7''" and insert -- 7''' --
Column 15, Line 38     delete "6''" and insert -- 6''' --
Column 15, Line 38     delete "7''" and insert -- 7''' --
Column 15, Line 40     delete "6''" and insert -- 6''' --
Column 15, Line 42     delete "5''" and insert -- 5''' --